(12) United States Patent
Peese et al.

(10) Patent No.: US 8,846,659 B2
(45) Date of Patent: Sep. 30, 2014

(54) HIV INTEGRASE INHIBITORS

(75) Inventors: Kevin Peese, Haddam, CT (US); B. Narasimhulu Naidu, Durham, CT (US); Manoj Patel, Berlin, CT (US); Chen Li, South Glastonbury, CT (US); Michael A. Walker, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 205 days.

(21) Appl. No.: 13/313,423

(22) Filed: Dec. 7, 2011

(65) Prior Publication Data

US 2012/0309745 A1 Dec. 6, 2012

Related U.S. Application Data

(60) Provisional application No. 61/421,919, filed on Dec. 10, 2010.

(51) Int. Cl.
*A61K 31/55* (2006.01)
*C07D 487/08* (2006.01)
*C07D 487/04* (2006.01)

(52) U.S. Cl.
CPC .................................. *C07D 487/04* (2013.01)
USPC ...................................... 514/214.02; 540/579

(58) Field of Classification Search
USPC ...................................... 514/214.02; 540/579
See application file for complete search history.

(56) References Cited

U.S. PATENT DOCUMENTS

| 7,745,453 | B2 | 6/2010 | Mikamiyama et al. |
| 8,129,398 | B2 | 3/2012 | Beaulieu et al. |
| 2012/0022045 | A1 | 1/2012 | Venkatraman et al. |

*Primary Examiner* — Brenda Coleman
(74) *Attorney, Agent, or Firm* — James Epperson

(57) ABSTRACT

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

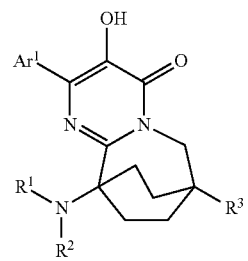

13 Claims, No Drawings

HIV INTEGRASE INHIBITORS

CROSS REFERENCE TO RELATED APPLICATIONS

This patent application claims the benefit of U.S. provisional patent application No. 61/421,919 filed Dec. 10, 2010.

BACKGROUND OF THE INVENTION

The disclosure generally relates to the novel compounds of formula I, including their salts, which inhibit HIV integrase and prevent viral integration into human DNA. This action makes the compounds useful for treating HIV infection and AIDS. The invention also encompasses pharmaceutical compositions and methods for treating those infected with HIV.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into four classes based on the viral protein they target and their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleoside reverse transcriptase inhibitors that behave as substrate mimics to halt viral cDNA synthesis. The non-nucleoside reverse transcriptase inhibitors, nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. Used alone these drugs are effective in reducing viral replication. There are also peptidomimetic protease inhibitors including saquinavir, indinavir, ritonavir, nelfinavir, amprenavir, lopinavir, darunavir, atazanavir, and tipranavir, and integrase inhibitors such as raltegravir. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Further, J.; Satten, G. A.; Aschman, D. J.; Holmberg, S. D. *N Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly, there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase is a component of the pre-integration complex of the virus that is assembled in the cell shortly after infection (Chiu, T. K.; Davies, D. R. *Curr. Top. Med. Chem.* 2004, 4, 965-977). This enzyme catalyzes the integration of proviral DNA into the host genome and is absolutely required for viral infectivity. Early experiments showed that mutating the active site of integrase within a proviral clone produces virus unable to replicate due to its inability to insert into the host chromosome (Englund, G.; Theodore, T. S.; Freed, E. O.; Engleman, A.; Martin, M. A. *J. Virol.* 1995, 69, 3216-3219). Selective HIV integrase inhibitors have been shown to possess effective anti-HIV activity in cell culture (Hazuda, D. J.; Felock, P.; Witmer, M.; Wolfe, A; Stillmock, K.; Grobler, J. A.; Espeseth, A.; Gabryelski, L.; Schleif, W.; Blau, C.; Miller, M. D. *Science,* 2000, 287, 646-650), and it is clear that this class of inhibitors is very effective as part of a combination regimen containing HIV inhibitors of different classes. An HIV integrase inhibitor, raltegravir (Isentress®), has been approved for use in treatment experienced patients based upon 48 week trial results (Cooper, D. A.; Gatell, J.; Rockstroh, J.; Katlama, C.; Yeni, P.; Lazzarin, A.; Xu, X.; Isaacs, R.; Teppler, H.; Nguyen, B. Y. *15th Conference on Retroviruses and Opportunistic Infections*, Boston, Mass., Feb. 3-6, 2008 Abst. 105LB: Evering, T. H.; Markowitz, M. *Drugs Today,* 2007, 43, 865-877). In addition, a second integrase inhibitor, elvitegravir (GS-9137), completed a successful Phase II trial in combination with ritonavir boosting in naive and treatment experienced patients (Zolopa, A. *14th Conference on Retroviruses and Opportunistic Infections*, Los Angeles, Calif. Feb. 25-28, 2007 Abst. 143LB). Thus, HIV-1 integrase is a promising target for novel anti-HIV-1 therapeutics.

HIV integrase inhibitors have been disclosed. See, for example, PCT patent application publications WO05/061501 and WO2010/088167.

The invention provides technical advantages, for example, the compounds are novel and inhibit HIV integrase. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention are compounds of Formula I

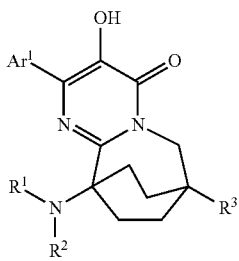

where:
R¹ is hydrogen, alkyl, alkylCO, (tetrahydropyranyl)CO, ((Ar²)alkyl)CO, ((Ar²)cycloalkyl)CO, (Ar²)CO, CO₂R⁴, CON(R⁵)(R⁶), COCO₂R⁴, or COCON(R⁵)(R⁶);
R² is hydrogen or alkyl;
R³ is hydrogen;
R⁴ is hydrogen, alkyl, or benzyl;
R⁵ is hydrogen, alkyl, cycloalkyl, haloalkyl, hydroxyalkyl, alkoxyalkyl aminoalkyl, alkylaminoalkyl, dialkylaminoalkyl, or alkylCO;
R⁶ is hydrogen, alkyl, cycloalkyl, haloalkyl, hydroxyalkyl, alkoxyalkyl aminoalkyl, alkylaminoalkyl, dialkylaminoalkyl, or alkylCO;
or N(R⁵)(R⁶) taken together is azetidinyl, pyrrolidinyl, piperidinyl, piperazinyl, or morpholinyl, and is substituted with 0-3 substituents selected from halo and alkyl;
Ar¹ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl; Ar¹ is substituted with 1 benzyl moiety which is further substituted with 0-3 substituents selected from halo and alkyl; and Ar¹ is substituted with 0-2 alkyl substituents; and
Ar² is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, alkoxy, N(R⁵)(R⁶), CO₂R⁴, and CON(R⁵)(R⁶);
or a pharmaceutically acceptable salt thereof.

Another aspect of the invention is a compound of formula I where
R¹ is hydrogen, ((Ar²)alkyl)CO, ((Ar²)cycloalkyl)CO, (Ar²)CO, or COCON(R⁵)(R⁶);
R² is hydrogen or alkyl;
R³ is hydrogen;
R⁵ is hydrogen, alkyl, or alkylCO;
R⁶ is hydrogen or alkyl;
or N(R⁵)(R⁶) taken together is pyrrolidinyl;
Ar¹ is triazolyl, oxadiazolyl, thiadiazolyl, imidazolyl, oxazolyl, or thiazolyl; Ar¹ is substituted with 1 benzyl moiety which is further substituted with 1 halo substituent; and
Ar² is triazolyl, pyrazolyl, isoxazolyl, pyridinyl, or pyridazinyl, and is substituted with 0-1 alkyl substituents;
or a pharmaceutically acceptable salt thereof.

Another aspect of the invention is a compound of formula I where R¹ is hydrogen, ((Ar²)(dimethyl)methyl)CO, ((Ar²)cyclopropyl)CO, (Ar²)CO, or COCON(R⁵)(R⁶); R² is hydrogen or methyl; R³ is hydrogen; R⁵ is methyl or acetyl; R⁶ is methyl; or N(R⁵)(R⁶) taken together is pyrrolidinyl; Ar¹ is triazolyl, oxadiazolyl, thiadiazolyl, imidazolyl, oxazolyl, or thiazolyl; Ar¹ is substituted with 1 p-fluorobenzyl; and Ar² is triazolyl, methylpyrazolyl, methylisoxazolyl, pyridinyl, or pyridazinyl; or a pharmaceutically acceptable salt thereof.

Another aspect of the invention is a compound of formula I where R¹ is ((Ar²)alkyl)CO, ((Ar²)cycloalkyl)CO, (Ar²)CO, or COCON(R⁵)(R⁶).

Another aspect of the invention is a compound of formula I where R¹ is ((Ar²)alkyl)CO, ((Ar²)cycloalkyl)CO, (Ar²)CO, or COCON(R⁵)(R⁶).

Another aspect of the invention is a compound of formula I where R¹ is COCON(R⁵)(R⁶).

Another aspect of the invention is a compound of formula I where R¹ is COCONMe₂.

Another aspect of the invention is a compound of formula I where Ar¹ is triazolyl, oxadiazolyl, thiadiazolyl, imidazolyl, oxazolyl, or thiazolyl, and Ar¹ is substituted with 1 benzyl moiety which is further substituted with 0-3 substituents selected from halo and alkyl.

Another aspect of the invention is a compound of formula I where Ar² is pyrazolyl or isoxazolyl, and is substituted with 0-1 alkyl substituents.

For a compound of Formula I, the scope of any instance of a variable substituent, including R¹, R², R³, R⁴, R⁵, R⁶, Ar¹, and Ar², can be used independently with the scope of any other instance of a variable substituent. As such, the invention includes combinations of the different aspects.

Unless specified otherwise, these terms have the following meanings. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents R¹ and R² of formula IV are intended to bond to the benzene ring of formula IV and not to the thiophene ring.

"Dioxothiazinyl" means

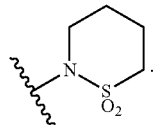

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. An example of a tautomeric pair is shown below.

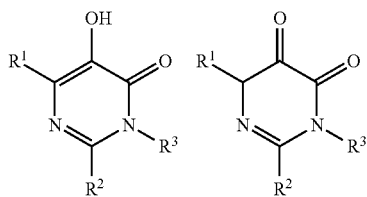

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Scheme 1

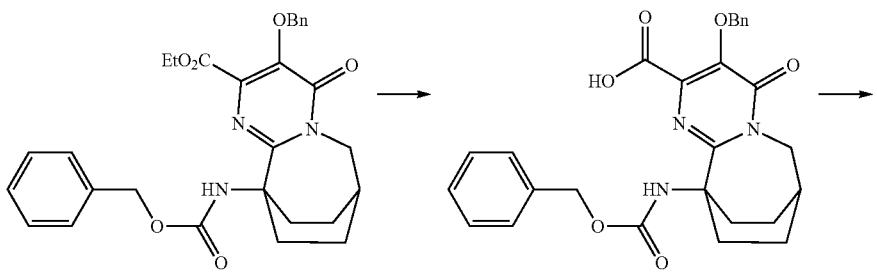

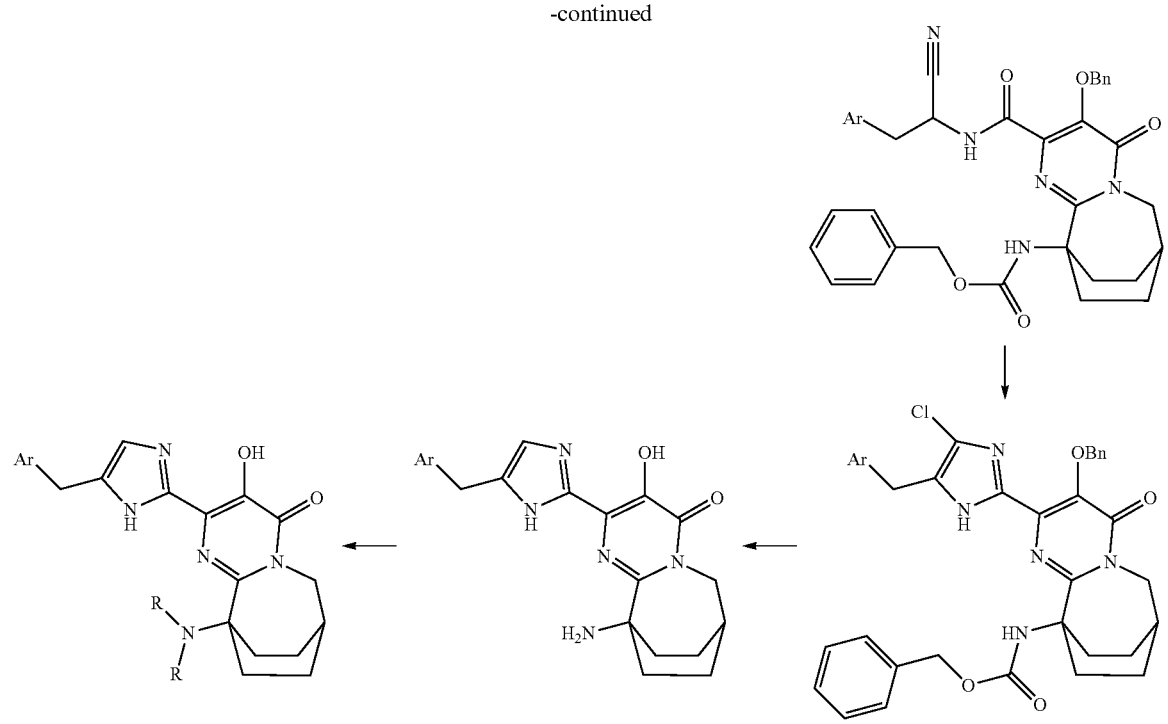
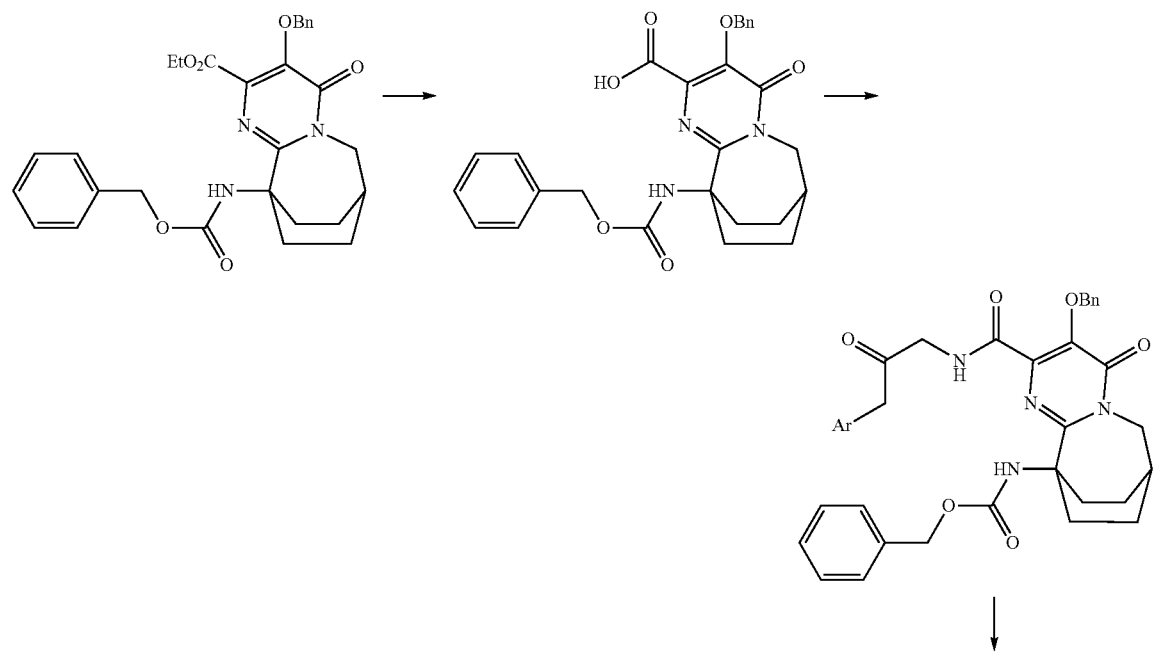
Scheme 2

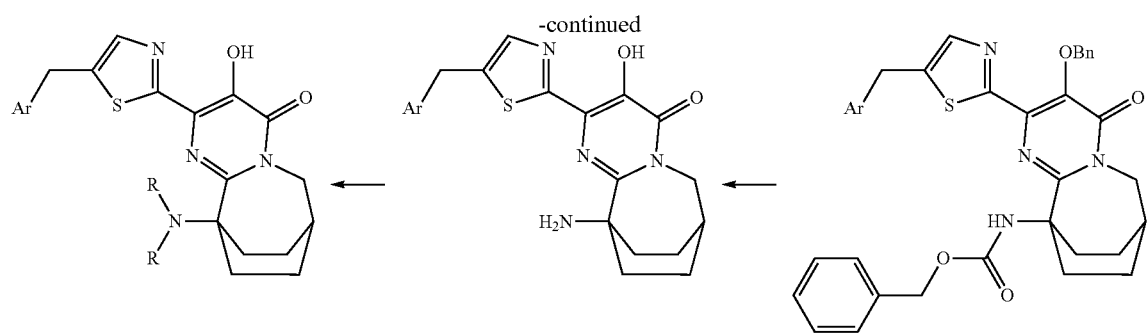
Scheme 3
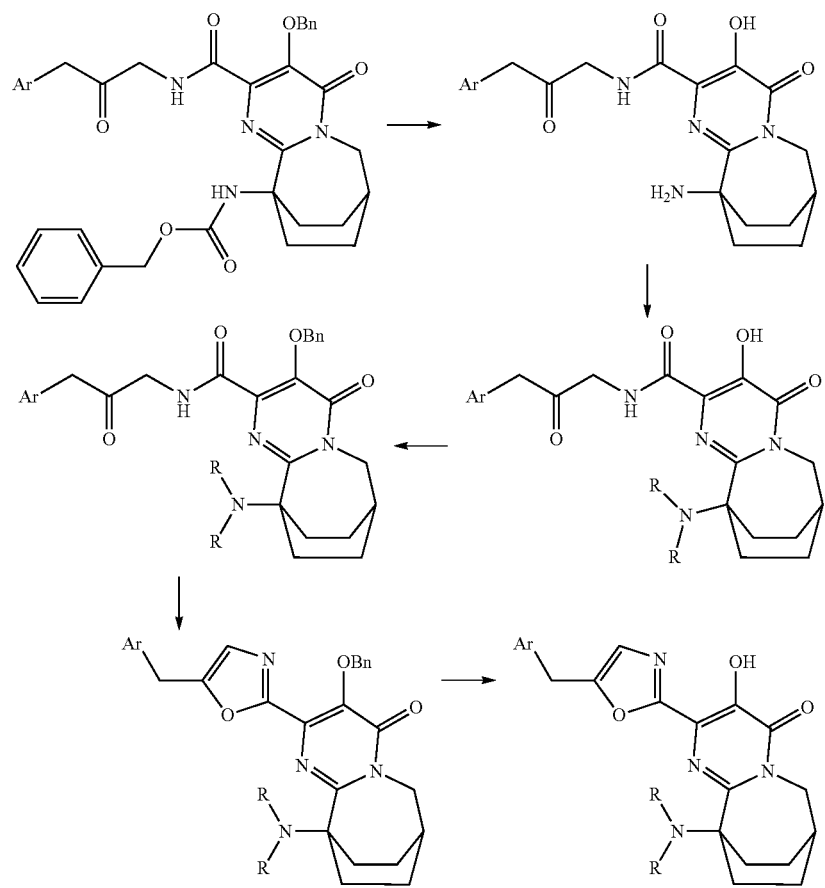

Scheme 4

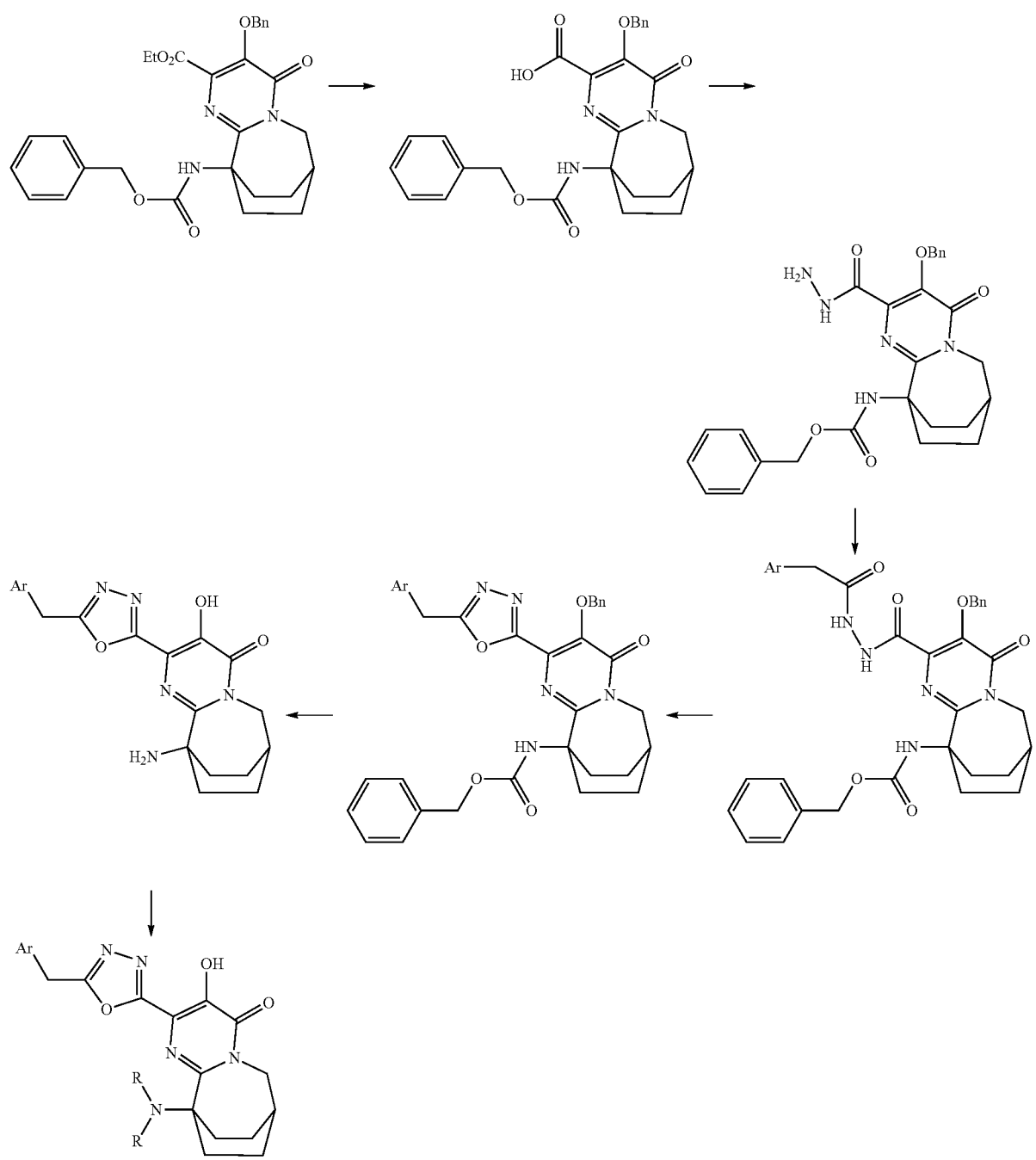

Biological Methods

HIV-Integrase Inhibition Activity.

Radiolabeled integrase inhibitor, BMS-641493 was used as a known reference ligand to determine the binding constants towards the integrase enzyme of the compounds described in this invention using a method similar to that described in; Dicker et al. *J. Biological Chem.* 2007, 282, 31186-31196; Dicker et al. *J. Biol. Chem.* 2008, 283, 23599-23609 and Dicker et al. *Biochemistry* 2008, 47, 13481-13488. BMS-641493 is a known active-site binding inhibitor as it can be competed off the Kd values for [3H]BMS-641493 were determined from fitting data to a saturation binding curve using Graphpad Prism, V4.01. The Ki measurement toward integrase was made by measuring the inhibition of binding of [3H]BMS-641493 to enzyme-SPA bead complexes in the presence of serial dilutions of the test compounds. The Ki value was determined from the [3H]BMS-641493 Kd and the inhibition binding curve using Graphpad Prism, V4.03. Results are shown in the Table 1.

TABLE 1

| Example | Activity μM |
|---|---|
| 2 | 0.021 |
| 3 | 0.122 |
| 4 | 0.021 |
| 5 | 3.880 |
| 6 | 0.400 |
| 7 | 0.222 |
| 8 | 0.115 |
| 9 | 1.074 |
| 10 | 0.009 |
| 11 | 0.019 |
| 12 | 0.013 |
| 13 | 0.013 |
| 14 | 0.041 |
| 15 | 0.057 |
| 16 | 1.469 |
| 17 | 0.010 |
| 18 | 0.016 |

Inhibition of HIV Replication.

A recombinant NL-Rluc virus was constructed in which a section of the nef gene from NL4-3 was replaced with the *Renilla* Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_H$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). the results from at least 2 experiments were used to calculate the $EC_{50}$ values. Results are shown in the Table 2.

TABLE 2

| Example | Activity μM |
|---|---|
| 1 | 0.021 |
| 2 | 0.005 |
| 3 | 0.018 |
| 4 | 0.008 |
| 5 | 0.060 |
| 6 | 0.001 |
| 7 | 0.002 |
| 8 | 0.0004 |
| 10 | 0.006 |
| 11 | 0.024 |
| 12 | 0.008 |
| 13 | 0.002 |
| 14 | 0.007 |
| 15 | 0.053 |
| 16 | 0.021 |
| 17 | 0.005 |
| 18 | 0.005 |

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. *Science* 2000, 287, 646). Recently reltegravir, an HIV integrase inhibitor, has been approved by the FDA for treating AIDS and HIV infection.

Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof.

Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences,* 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement. A partial list of such agents is shown in the table below.

| Drug Name | Manufacturer | Indication |
|---|---|---|
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec- J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, Sustiva ®) (-)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |

| Drug Name | Manufacturer | Indication |
|---|---|---|
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Emtriva ® (Emtricitabine) (FTC) | Gilead | HIV infection, AIDS, (reverse transcriptase inhibitor) |
| Combivir ® | GSK | HIV infection, AIDS, (reverse transcriptase inhibitor) |
| Abacavir succinate (or Ziagen ®) | GSK | HIV infection, AIDS, (reverse transcriptase inhibitor) |
| Reyataz ® (or atazanavir) | Bristol-Myers Squibb | HIV infection AIDs, protease inhibitor |
| Fuzeon ® (Enfuvirtide or T-20) | Roche/Trimeris | HIV infection AIDs, viral Fusion inhibitor |
| Lexiva® (or Fosamprenavir calcium) | GSK/Vertex | HIV infection AIDs, viral protease inhibitor |
| Selzentry Maraviroc; (UK 427857) | Pfizer | HIV infection AIDs, (CCR5 antagonist, in development) |
| Trizivir ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| Truvada ® | Gilead | Combination of Tenofovir disoproxil fumarate salt (Viread ®) and Emtriva ® (Emtricitabine) |
| Integrase Inhibitor GS917/JTK-303 Elvitegravir | Gilead/Japan Tobacco | HIV Infection AIDS in development |
| Triple drug combination Atripla ® | Gilead/Bristol-Myers Squibb | Combination of Tenofovir disoproxil fumarate salt (Viread ®), Emtriva ® (Emtricitabine), and Sustiva ® (Efavirenz) |
| Festinavir ® | Oncolys BioPharma | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |

| Drug Name | Manufacturer | Indication |
|---|---|---|
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

DESCRIPTION OF SPECIFIC EMBODIMENTS

Abbreviations used in the schemes generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "cc" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

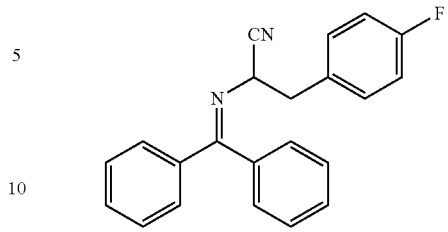

Intermediate 1

2-(Diphenylmethyleneamino)-3-(4-fluorophenyl)propanenitrile (Procedure adapted from *J. Org. Chem.* 2003, 68, 50-54). To a solution of 2-(diphenylmethyleneamino)acetonitrile (1.21 g, 5.47 mmol, 1.0 equiv) in CH$_2$Cl$_2$ (9.12 mL) was added 4-fluorobenzyl bromide (0.75 mL, 6.02 mmol, 1.1 equiv), benzyltrimethylammonium chloride (0.10 g, 0.547 mmol, 0.1 equiv), and NaOH (0.99 mL of a 10 M aqueous solution, 9.85 mmol, 1.8 equiv). The reaction was stirred vigorously for 18 h, at which time TLC analysis indicated complete consumption of the starting nitrile. The reaction was added to water and extracted with CH$_2$Cl$_2$ (×3). The combined CH$_2$Cl$_2$ extracts were dried (Na$_2$SO$_4$) and concentrated in vacuo. The crude product was purified by silica gel chromatography (5-30% ethyl acetate/hexane) to provide the title compound (1.65 g, 92% yield) as a viscous yellow oil. $^1$H NMR (400 MHz, CDCl$_3$) δ ppm 7.54-7.65 (m, 2H), 7.38-7.48 (m, 4H), 7.31-7.38 (m, 2H), 7.00-7.09 (m, 2H), 6.89-6.97 (m, 2H), 6.84 (d, J=6.30 Hz, 2H), 4.35 (dd, J=7.81, 6.04 Hz, 1H), 3.10-3.29 (m, 2H); LCMS (ES+, (M+H)$^+$) m/z 329.25.

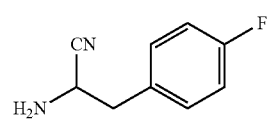

Intermediate 2

2-Amino-3-(4-fluorophenyl)propanenitrile hydrochloride

To a solution of 2-(diphenylmethyleneamino)-3-(4-fluorophenyl)propanenitrile, intermediate 1 (1.65 g, 5.02 mmol, 1.0 equiv) in THF (20.1 mL) was added HCl (5.53 mL of a 1 M aqueous solution, 5.53 mmol, 1.1 equiv). After stirring 3 h, the reaction was poured into water and washed with ether (×3). The aqueous layer was neutralized by the addition of 10 M NaOH and extracted with CH$_2$Cl$_2$ (×3). The combined CH$_2$Cl$_2$ extracts were dried (Na$_2$SO$_4$) and then concentrated in vacuo to provide the title compound (0.77 g, 93% yield) as a colorless oil. For convenience, the amine could be converted into the hydrochloride salt by dissolution in ether, treating with 2 M HCl in ether, and filtering the resulting white solid: $^1$H NMR (400 MHz, CDCl$_3$) δ ppm 7.24-7.29 (m, 2H), 7.01-7.08 (m, 2H), 3.85-3.96 (m, 1H), 2.92-3.07 (m, 2H), 1.60 (d, J=7.55 Hz, 2H).

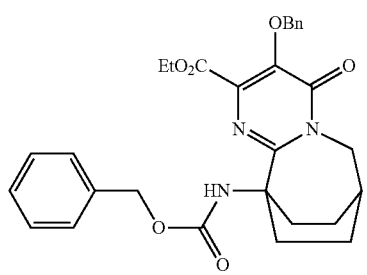

Intermediate 3

Ethyl 3-(benzyloxy)-10-(((benzyloxy)carbonyl)amino)-4-oxo-4,6,7,8,9,10-hexahydro-7,10-ethanopyrimido[1,2-a]azepine-2-carboxylate To a solution of ethyl 10-(((benzyloxy)carbonyl)amino)-3-hydroxy-4-oxo-4,6,7,8,9,10-hexahydro-7,10-ethanopyrimido[1,2-a]azepine-2-carboxylate (prepared according to the procedure in WO2009117540) (500 mg, 1.170 mmol) in DMF (20 mL) was added $K_2CO_3$ (323 mg, 2.339 mmol) followed by benzyl bromide (0.208 mL, 1.755 mmol) and the resulting mixture was heated at 50° C. for 16 h. After cooling to room temp, water was added and the mixture was extracted with ethyl acetate, dried ($Na_2SO_4$), filtered and concentrated. The crude product was purified by silica gel chromatography (20-100% ethyl acetate/hexane to afford the title compound (250 mg, 42% yield) as a light yellow liquid. $^1$H NMR (500 MHz, $CDCl_3$) δ: 7.47 (d, 2H, J=7.02 Hz), 7.32-7.39 (m, 8H), 7.19 (brs, 1H), 5.26 (s, 2H), 5.08 (s, 2H), 4.31 (q, 2H, J=7.02 Hz), 4.13 (d, 2H, J=3.97 Hz), 2.87-2.96 (m, 2H), 2.46 (brs, 1H), 1.94-2.03 (m, 2H), 1.80-1.89 (m, 2H), 1.65-1.75 (m, 2H), 1.29 (t, 3H, J=7.32 Hz). LCMS (M+H)=518.28.

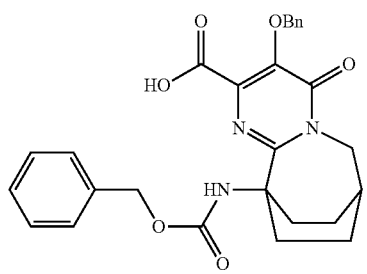

Intermediate 4

3-(Benzyloxy)-10-(((benzyloxy)carbonyl)amino)-4-oxo-4,6,7,8,9,10-hexahydro-7,10-ethanopyrimido[1,2-a]azepine-2-carboxylic acid To a solution of ethyl 3-(benzyloxy)-10-(((benzyloxy)carbonyl)amino)-4-oxo-4,6,7,8,9,10-hexahydro-7,10-ethanopyrimido[1,2-a]azepine-2-carboxylate, Intermediate 3 (250 mg, 0.483 mmol) in EtOH (5 mL) was added water (1.250 mL) followed by LiOH—$H_2O$ (20.27 mg, 0.483 mmol) and the mixture was stirred at room temp for 16 h. Water (10 mL) was then added and the mixture was extracted with ether (100 mL). The aqueous layer was then acidified with 1N HCl and then extracted with ethyl acetate (2×100 mL), washed with brine, dried ($Na_2SO_4$), filtered and concentrated to afford the title compound (180 mg, 76% yield) as a light yellow solid. $^1$H NMR (500 MHz, $CDCl_3$) δ: 7.51 (d, 2H, J=6.71 Hz), 7.30-7.40 (m, 9H), 5.46 (s, 2H), 5.06 (s, 2H), 4.10-4.15 (m, 2H), 2.47-2.61 (m, 3H), 2.03-2.11 (m, 2H), 1.91-2.01 (m, 2H), 1.63-1.73 (m, 2H). LCMS (M+H)=490.23.

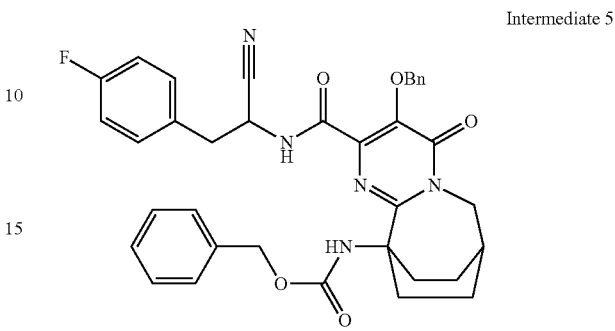

Intermediate 5

Benzyl(3-(benzyloxy)-2-((1-cyano-2-(4-fluorophenyl)ethyl)carbamoyl)-4-oxo-6,7,8,9-tetrahydro-7,10-ethanopyrimido[1,2-a]azepin-10(4H)-yl)carbamate To a solution of 3-(benzyloxy)-10-(((benzyloxy)carbonyl)amino)-4-oxo-4,6,7,8,9,10-hexahydro-7,10-ethanopyrimido[1,2-a]azepine-2-carboxylic acid, Intermediate 4 (180 mg, 0.368 mmol) in $CH_2Cl_2$ (2 mL) was added oxalyl chloride (0.051 mL, 0.588 mmol) followed by 1 drop of DMF. After stirring for 2 h, the mixture was concentrated under reduced pressure. The crude acid chloride was then diluted with dichloromethane (2 mL) and added to a stirred solution of 2-amino-3-(4-fluorophenyl)propanenitrile HCl (81 mg, 0.404 mmol) and triethylamine (0.205 mL, 1.471 mmol) in $CH_2Cl_2$ (2 mL) and the resulting solution was stirred at room temperature. After 16 h at room temperature, the reaction mixture was poured into sat. $NaHCO_3$ and extracted with dichloromethane (50 mL×3), dried ($Na_2SO_4$), filtered and concentrated to give a yellow oil. The crude product was then purified by silica gel chromatography (50-100% EtOAc/hexane) to afford the title compound (145 mg, 62% yield) as a light yellow solid. $^1$H NMR (500 MHz, $CDCl_3$) δ: 7.82 (brs, 1H), 7.28-7.49 (m, 10H), 7.06-7.17 (m, 2H), 6.96 (t, 2H, J=8.39 Hz), 6.63 (brs, 1H), 5.27-5.40 (m, 2H), 5.00-5.14 (m, 2H), 4.07-4.14 (m, 3H), 2.77-2.92 (m, 2H), 2.64-2.78 (m, 2H), 2.49 (brs, 1H), 1.87-2.02 (m, 4H), 1.63-1.75 (m, 2H). LCMS (M+H)=636.19.

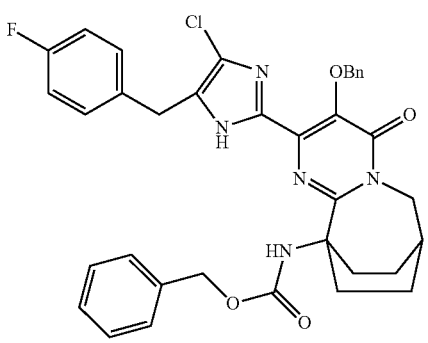

Intermediate 6

Benzyl(3-(benzyloxy)-2-(4-chloro-5-(4-fluorobenzyl)-1H-imidazol-2-yl)-4-oxo-6,7,8,9-tetrahydro-7,10-ethanopyrimido[1,2-a]azepin-10(4H)-yl)carbamate To a solution of benzyl(3-(benzyloxy)-2-((1-cyano-2-(4-fluorophenyl)ethyl)carbamoyl)-4-oxo-6,7,8,9-tetrahydro-7,10-ethanopyrimido[1,2-a]azepin-10(4H)-yl)carbamate, Intermediate 5 (140 mg, 0.220 mmol) in acetonitrile (4 mL) was added carbon tetrachloride (0.053 mL, 0.551 mmol), followed by triphenylphosphine (144 mg, 0.551 mmol) and the mixture was heated at 45° C. After stirring for 16 h, the mixture was cooled to room temp and concentrated in vacuo. The residue was then treated with dichloromethane (10 mL) and 0.5 N NaOH (20 mL). The mixture was then poured into water and extracted with dichloromethane (×4), dried (Na$_2$SO$_4$), filtered and concentrated. The crude product was then purified by silica gel chromatography (40-100% EtOAc/hexane) to afford the title compound (90 mg, 42% yield) as a yellow solid. $^1$H NMR (500 MHz, CDCl$_3$) δ ppm 1.65-1.74 (m, 2H) 1.92-2.03 (m, 4H) 2.47 (br. s., 1H) 2.71-2.86 (m, 2H) 3.74 (s, 2H) 4.13 (d, J=3.66 Hz, 2H) 5.12 (s, 2H) 5.29 (s, 2H) 6.92 (d, J=7.63 Hz, 4H) 7.08 (br. s., 1H) 7.29-7.37 (m, 8H) 7.39-7.46 (m, 2H) 10.08 (br. s., 1H). (M+H)=654.28.

Intermediate 7

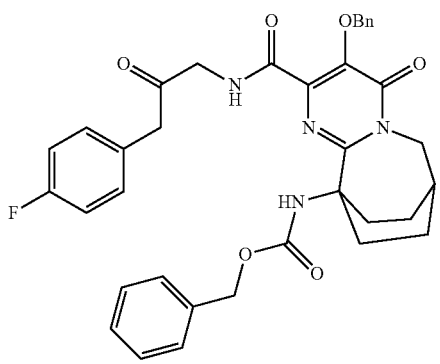

Benzyl(3-(benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)carbamate To a solution of 3-(benzyloxy)-10-(((benzyloxy)carbonyl)amino)-4-oxo-4,6,7,8,9,10-hexahydro-7,10-ethanopyrimido[1,2-a]azepine-2-carboxylic acid, Intermediate 4 (400 mg, 0.817 mmol) in CH$_2$Cl$_2$ (8 mL) was added oxalyl chloride (0.114 mL, 1.307 mmol) followed by 1 drop of DMF. After stirring for 2 h, the mixture was concentrated under reduced pressure. The crude acid chloride was then diluted with dichloromethane (5 mL)) and added to a stirred solution of 1-amino-3-(4-fluorophenyl)propan-2-one HCl (183 mg, 0.899 mmol) and triethylamine (0.456 mL, 3.27 mmol) in CH$_2$Cl$_2$ (8.00 mL) and the resulting solution stirred at room temperature. After 16 h the reaction mixture was poured into sat. NaHCO$_3$ and extracted with dichloromethane (50 mL×3), dried (Na$_2$SO$_4$), filtered and concentrated to give a yellow oil. The crude product was then purified by silica gel chromatography (50-100% EtOAc/hexane) to afford the title compound (400 mg, 0.626 mmol, 77% yield) as a light yellow solid. $^1$H NMR (500 MHz, CDCl$_3$) δ ppm 7.99 (1H, br. s.), 7.49 (2H, d, J=5.80 Hz), 7.28-7.37 (8H, m), 7.15 (2H, dd, J=8.55, 5.49 Hz), 7.01-7.04 (2H, m), 6.79 (1H, br. s.), 5.32 (2H, s), 5.06 (2H, s), 4.17 (2H, d, J=4.88 Hz), 4.12 (2H, d, J=3.66 Hz), 3.69 (2H, s), 2.67-2.78 (2H, m), 2.47 (1H, br. s.), 1.89-2.01 (4H, m), 1.64-1.72 (2H, m). LCMS (M+H)=640.04.

Intermediate 8

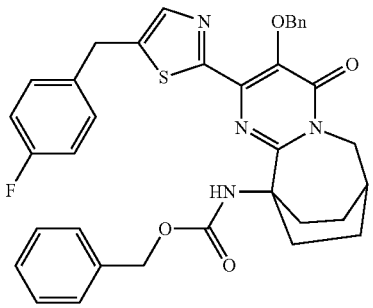

Benzyl(3-(benzyloxy)-2-(5-(4-fluorobenzyl)-1,3-thiazol-2-yl)-4-oxo-6,7,8,9-tetrahydro-7,10-ethanopyrimido[1,2-a]azepin-10(4H)-yl)carbamate To a solution of benzyl(3-(benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)carbamate, Intermediate 7 (120 mg, 0.188 mmol) in toluene was added Lawesson's Reagent (76 mg, 0.188 mmol) and stirred for 15 min at room temperature, 30 min at 60° C. and 2 h at 100° C. The resulting clear yellow mixture was then cooled, concentrated and purified by preparative HPLC to provide the title compound (60 mg, 0.094 mmol, 50.2% yield) as a yellow solid. $^1$H NMR (400 MHz, CDCl$_3$) δ ppm 7.79 (1H, s), 7.47-7.52 (2H, m), 7.29-7.39 (8H, m), 7.17 (2H, dd, J=8.28, 5.27 Hz), 6.94-7.07 (3H, m), 5.38 (2H, s), 5.09 (2H, s), 4.09-4.19 (4H, m), 2.69-2.84 (2H, m), 2.49 (1H, br. s.), 1.94-2.04 (4H, m), 1.65-1.76 (2H, m). LCMS (M+H)=637.27.

Intermediate 9

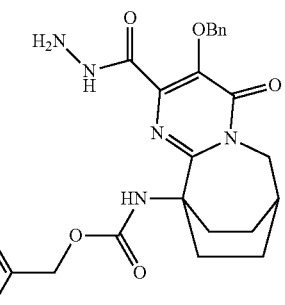

Benzyl(3-(benzyloxy)-2-(hydrazinylcarbonyl)-4-oxo-6,7,8,9-tetrahydro-7,10-ethanopyrimido[1,2-a]azepin-10(4H)-yl)carbamate To a solution of 3-(benzyloxy)-10-(((benzyloxy)carbonyl)amino)-4-oxo-4,6,7,8,9,10-hexahydro-7,10-ethanopyrimido[1,2-a]azepine-2-carboxylic acid, Intermediate 4 (1 g, 2.043 mmol) in CH$_2$Cl$_2$ (20 mL) was added oxalyl chloride (0.286 mL, 3.27 mmol). A few drops of DMF were added and the mixture stirred at room temperature for 2 h. Solvent was then removed under reduced pressure. The crude acid chloride was then diluted with dichloromethane (10 mL)) and added to a stirred solution of hydrazine (0.641 mL, 20.43 mmol) and triethylamine (2.85 mL, 20.43 mmol) in CH$_2$Cl$_2$ (20 mL) and the resulting solution stirred at room temperature. After 16 h the reaction mixture was poured into sat. NaHCO$_3$ and extracted with dichloromethane (50 mL×3), dried (Na$_2$SO$_4$), filtered and concentrated to give a yellow oil which was used in the next step without further purification. LCMS (M+H)=504.10.

Intermediate 10

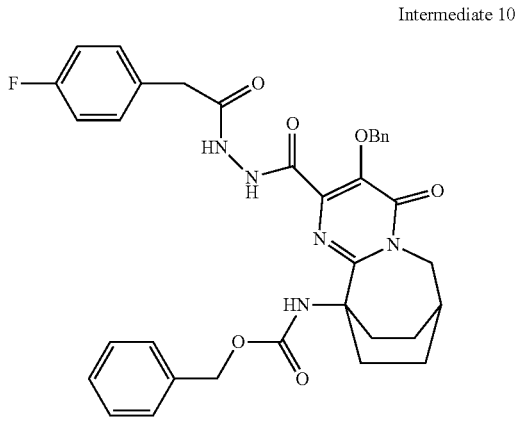 [SMILES: O=C(Cc1ccc(F)cc1)NNC(=O)c1nc2n(c(=O)c1OCc1ccccc1)CC1CCC2(NC(=O)OCc2ccccc2)CC1]

Benzyl(3-(benzyloxy)-2-((2-((4-fluorophenyl)acetyl)hydrazinyl)carbonyl)-4-oxo-6,7,8,9-tetrahydro-7,10-ethanopyrimido[1,2-a]azepin-10(4H)-yl)carbamate To a solution of benzyl(3-(benzyloxy)-2-(hydrazinylcarbonyl)-4-oxo-6,7,8,9-tetrahydro-7,10-ethanopyrimido[1,2-a]azepin-10(4H)-yl)carbamate, Intermediate 9 (400 mg, 0.794 mmol) in CH$_2$Cl$_2$ (15 mL) at 0° C. was added triethylamine (0.221 mL, 1.589 mmol) followed by 2-(4-fluorophenyl)acetyl chloride (0.098 mL, 0.715 mmol) and the resulting mixture stirred for 1 h. The mixture was allowed to warm to room temp and stirred for 3 h. The mixture was then concentrated and purified by preparative HPLC to afford the title compound (70 mg, 0.109 mmol, 13.78% yield) as a white solid. $^1$H NMR (500 MHz, CDCl$_3$) δ ppm 10.00 (1H, br. s.), 8.35 (1H, br. s.), 7.48-7.53 (2H, m), 7.27-7.38 (10H, m), 7.00-7.07 (2H, m), 6.55 (1H, br. s.), 5.39 (2H, s), 5.05 (2H, s), 4.10 (2H, d, J=3.36 Hz), 3.60 (2H, s), 2.56-2.70 (2H, m), 2.47 (1H, br. s.), 1.88-2.04 (4H, m), 1.59-1.71 (2H, m). LCMS (M+H)=640.35.

Intermediate 11

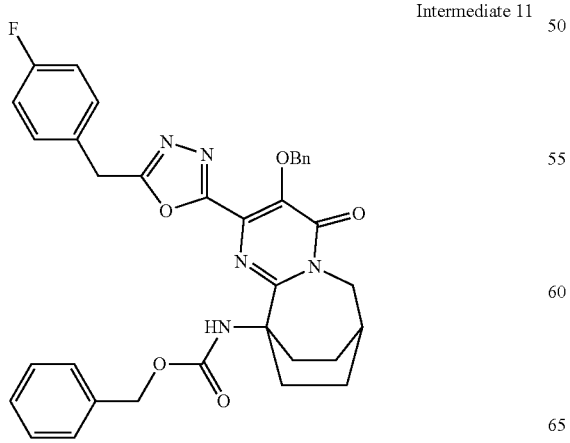

Benzyl(3-(benzyloxy)-2-(5-(4-fluorobenzyl)-1,3,4-oxadiazol-2-yl)-4-oxo-6,7,8,9-tetrahydro-7,10-ethanopyrimido[1,2-a]azepin-10(4H)-yl)carbamate To a stirred solution of benzyl(3-(benzyloxy)-2-((2-((4-fluorophenyl)acetyl)hydrazinyl)carbonyl)-4-oxo-6,7,8,9-tetrahydro-7,10-ethanopyrimido[1,2-a]azepin-10(4H)-yl) carbamate, Intermediate 10 (70 mg, 0.109 mmol), Ph$_3$P (51.7 mg, 0.197 mmol), N,N-diisopropylethylamine (0.115 mL, 0.657 mmol) in acetonitrile (3 mL) was added hexachloroethane (0.016 mL, 0.142 mmol). After 16 h the resulting mixture was purified by preparative HPLC to afford the title compound (30 mg, 0.048 mmol, 44.1% yield) as an off-white solid. $^1$H NMR (500 MHz, CDCl$_3$) δ ppm 7.45-7.48 (2H, m), 7.32-7.41 (8H, m), 7.21-7.26 (2H, m), 7.09 (1H, br. s.), 6.95 (2H, t, J=8.55 Hz), 5.40 (2H, s), 5.13 (2H, s), 4.19 (2H, s), 4.18 (2H, d, J=3.66 Hz), 2.87-2.96 (2H, m), 2.52 (1H, br. s.), 1.98-2.08 (2H, m), 1.87-1.95 (2H, m), 1.69-1.78 (2H, m). LCMS (M+H)=622.33.

Intermediate 12

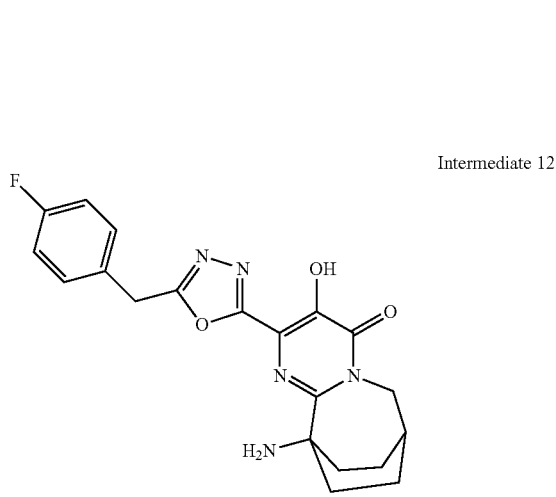 [SMILES: NC12CCC(CC1)Cn1c2nc(-c2nnc(Cc3ccc(F)cc3)o2)c(O)c1=O]

10-Amino-2-(5-(4-fluorobenzyl)-1,3,4-oxadiazol-2-yl)-3-hydroxy-7,8,9,10-tetrahydro-7,10-ethanopyrimido[1,2-a]azepin-4(6H)-one To a mixture of benzyl(3-(benzyloxy)-2-(5-(4-fluorobenzyl)-1,3,4-oxadiazol-2-yl)-4-oxo-6,7,8,9-tetrahydro-7,10-ethanopyrimido[1,2-a]azepin-10(4H)-yl)carbamate, Intermediate 11 (30 mg, 0.048 mmol) in CH$_2$Cl$_2$ (2 mL) was added HBr in acetic acid (0.218 mL, 1.206 mmol) and the mixture stirred at room temperature for 16 h. The mixture was concentrated and dried under high vacuum to afford the title compound (18 mg, 0.038 mmol, 78% yield) as a brown solid. $^1$H NMR (500 MHz, MeOD) δ ppm 7.39-7.46 (2H, m), 7.08-7.14 (2H, m), 4.38 (2H, s), 4.20 (2H, d, J=3.66 Hz), 2.60 (1H, br. s.), 2.22-2.31 (2H, m), 2.05-2.18 (4H, m), 1.85-1.94 (2H, m). LCMS (M+H)=398.18.

Intermediate 13

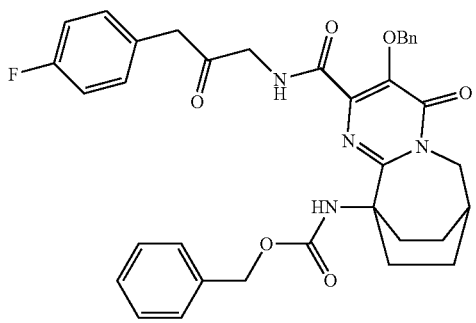

Benzyl(3-(benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)carbamate To a solution of 3-(benzyloxy)-10-(((benzyloxy)carbonyl)amino)-4-oxo-4,6,7,8,9,10-hexahydro-7,10-ethanopyrimido[1,2-a]azepine-2-carboxylic acid, Intermediate 4 (1 g, 2.043 mmol) in CH$_2$Cl$_2$ (20 mL) was added oxalyl chloride (0.286 mL, 3.27 mmol). A few drops of DMF was then added and the mixture stirred at room temperature for 2 h. Solvent was removed under reduced pressure and the crude acid chloride was diluted with dichloromethane (10 mL) and added to a stirred solution of 1-amino-3-(4-fluorophenyl)propan-2-one HCl (0.458 g, 2.247 mmol) and triethylamine (1.139 mL, 8.17 mmol) in CH$_2$Cl$_2$ (20 mL). The resulting solution was stirred at room temperature for 16 h then poured into sat. NaHCO$_3$ and extracted with dichloromethane (50 mL×3), dried (Na$_2$SO$_4$), filtered and concentrated to give a yellow oil. The crude product was then purified by silica gel chromatography (50-100% EtOAc/hexane) to afford the title compound (770 mg, 1.206 mmol, 59.0% yield) as a light yellow solid. $^1$H NMR (500 MHz, CDCl$_3$) δ ppm 7.99 (1H, br. s.), 7.49 (2H, d, J=5.80 Hz), 7.28-7.37 (8H, m), 7.15 (2H, dd, J=8.55, 5.49 Hz), 7.01-7.04 (2H, m), 6.79 (1H, br. s.), 5.32 (2H, s), 5.06 (2H, s), 4.17 (2H, d, J=4.88 Hz), 4.12 (2H, d, J=3.66 Hz), 3.69 (2H, s), 2.67-2.78 (2H, m), 2.47 (1H, br. s.), 1.89-2.01 (4H, m), 1.64-1.72 (2H, m). LCMS (M+H)=640.04.

Intermediate 14

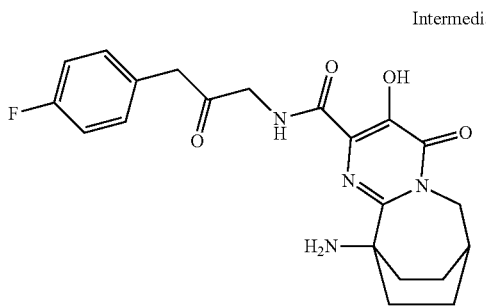

10-Amino-N-(3-(4-fluorophenyl)-2-oxopropyl)-3-hydroxy-4-oxo-4,6,7,8,9,10-hexahydro-7,10-ethanopyrimido[1,2-a]azepine-2-carboxamide To a mixture of benzyl(3-(benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)carbamate, Intermediate 13 (540 mg, 0.845 mmol) in MeOH (8 mL) was added 1N HCl (0.930 mL, 0.930 mmol) followed by 10% Pd/C (90 mg, 0.085 mmol) and the mixture stirred under a hydrogen atmosphere for 2 h. The mixture was then filtered and thoroughly washed with ethyl acetate. The filtrate was concentrated in vacuo and dried under high vacuum overnight to afford the title compound (318 mg, 0.705 mmol, 83% yield) as an off-white solid. $^1$H NMR (500 MHz, DMSO-d$_6$) δ ppm 12.07 (1H, br. s.), 9.61 (1H, t, J=5.95 Hz), 7.24-7.30 (2H, m), 7.13-7.20 (2H, m), 4.33 (2H, d, J=6.10 Hz), 4.00 (2H, d, J=3.66 Hz), 3.92 (2H, s), 2.46 (1H, br. s.), 2.01-2.13 (4H, m), 1.79-1.88 (2H, m), 1.68-1.77 (2H, m). LCMS (M+H)=415.15.

Intermediate 15

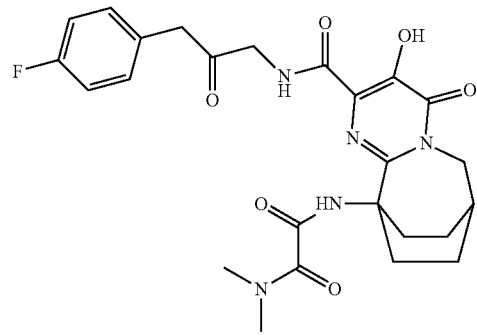

N'-(2-((3-(4-Fluorophenyl)-2-oxopropyl)carbamoyl)-3-hydroxy-4-oxo-6,7,8,9-tetrahydro-7,10-ethanopyrimido[1,2-a]azepin-10(4H)-yl)-N,N-dimethylethanediamide To a solution of 10-amino-N-(3-(4-fluorophenyl)-2-oxopropyl)-3-hydroxy-4-oxo-4,6,7,8,9,10-hexahydro-7,10-ethanopyrimido[1,2-a]azepine-2-carboxamide, Intermediate 14 (318 mg, 0.705 mmol) in DMF (8 mL) were added 2-(dimethylamino)-2-oxoacetic acid (165 mg, 1.411 mmol), N,N-diisopropylethylamine (0.739 mL, 4.23 mmol), HATU (536 mg, 1.411 mmol) and DMAP (17.23 mg, 0.141 mmol) and the resulting mixture was stirred at room temperature for 3 h. The mixture was then purified by preparative HPLC to afford the title compound (210 mg, 0.409 mmol, 58.0% yield) as an off-white solid. $^1$H NMR (500 MHz, CDCl$_3$) δ ppm 11.67 (1H, br. s.), 8.54 (1H, t, J=5.49 Hz), 8.03 (1H, s), 7.19 (2H, dd, J=8.55, 5.19 Hz), 6.99-7.05 (2H, m), 4.26 (2H, d, J=5.49 Hz), 4.17 (2H, d, J=3.97 Hz), 3.77 (2H, s), 3.28 (3H, s), 2.92 (3H, s), 2.46-2.57 (5H, m), 2.09-2.17 (2H, m), 1.91-2.01 (2H, m), 1.67-1.77 (2H, m). LCMS (M+H)=514.26.

Intermediate 16

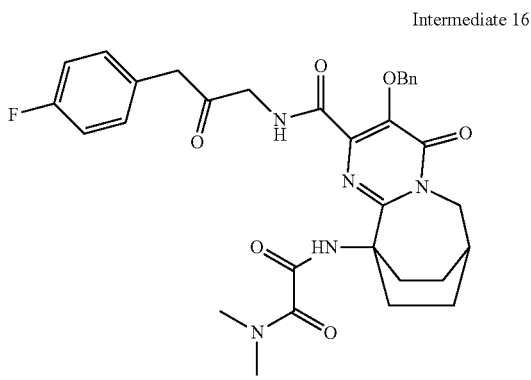 [SMILES: CN(C)C(=O)C(=O)NC12CCC(CC1)Cn1c2nc(C(=O)NCC(=O)Cc2ccc(F)cc2)c(OCc2ccccc2)c1=O]

N'-(3-(Benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)-N,N-dimethylethanediamide To a mixture of N'-(2-((3-(4-fluorophenyl)-2-oxopropyl)carbamoyl)-3-hydroxy-4-oxo-6,7,8,9-tetrahydro-7,10-ethanopyrimido[1,2-a]azepin-10(4H)-yl)-N,N-dimethylethanediamide, Intermediate 15 (140 mg, 0.273 mmol) in DMF (5 mL) was added K$_2$CO$_3$ (67.8 mg, 0.491 mmol) followed by (bromomethyl)benzene (0.049 mL, 0.409 mmol) and the resulting mixture stirred at room temp for 16 h. Water was then added and the mixture was extracted with ethyl acetate (2×50 mL), dried (Na$_2$SO$_4$), filtered and concentrated. The crude product was purified by silica gel chromatography to afford the title compound (140 mg, 0.162 mmol, 59.5% yield) as a yellow oil. $^1$H NMR (500 MHz, CDCl$_3$) δ ppm 8.73 (1H, s), 8.31 (1H, s), 7.53-7.59 (2H, m), 7.31-7.38 (3H, m), 7.18-7.24 (2H, m), 7.02-7.07 (2H, m), 5.35 (2H, s), 4.73 (2H, s), 4.29 (2H, d, J=5.49 Hz), 4.16 (2H, d, J=3.66 Hz), 2.94 (3H, s), 2.91 (3H, s), 2.70-2.79 (2H, m), 2.53 (1H, br. s.), 1.98-2.12 (4H, m), 1.70-1.80 (2H, m). LCMS (M+H)=604.31.

Intermediate 17

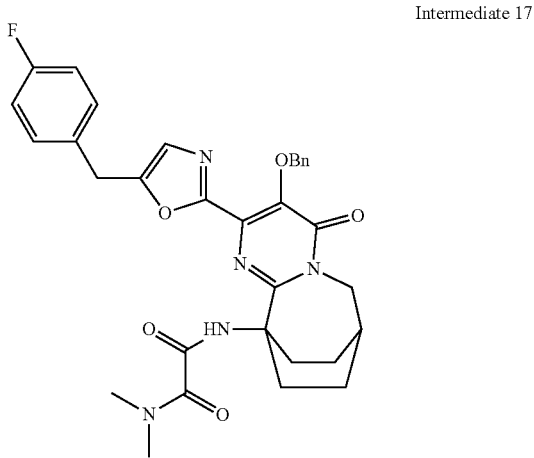 [SMILES: CN(C)C(=O)C(=O)NC12CCC(CC1)Cn1c2nc(-c2ncc(Cc3ccc(F)cc3)o2)c(OCc2ccccc2)c1=O]

N'-(3-(Benzyloxy)-2-(5-(4-fluorobenzyl)-1,3-oxazol-2-yl)-4-oxo-6,7,8,9-tetrahydro-7,10-ethanopyrimido[1,2-a]azepin-10(4H)-yl)-N,N-dimethylethanediamide To a mixture of N'-(3-(benzyloxy)-2-((3-(4-fluorophenyl)-2-oxopropyl)carbamoyl)-4-oxo-6,7,8,9-tetrahydro-7,10-ethanopyrimido[1,2-a]azepin-10(4H)-yl)-N,N-dimethylethanediamide, Intermediate 16 (125 mg, 0.207 mmol) in THF (8 mL) was added Burgess Reagent (345 mg, 1.450 mmol) and the mixture heated to reflux for 5 h. The mixture was then cooled, concentrated and purified by preparative HPLC to afford the title compound (65 mg, 0.111 mmol, 53.6% yield) as a white solid. $^1$H NMR (500 MHz, CDCl$_3$) δ ppm 9.24 (1H, s), 7.38-7.42 (2H, m), 7.30-7.34 (3H, m), 7.18-7.23 (2H, m), 7.11 (1H, s), 6.99-7.04 (2H, m), 5.38 (2H, s), 4.18 (2H, d, J=3.66 Hz), 4.02 (2H, s), 3.30 (3H, s), 3.03 (3H, s), 2.88-2.96 (2H, m), 2.54 (1H, br. s.), 1.94-2.10 (4H, m), 1.71-1.80 (2H, m). LCMS (M+H)=586.31.

Example 1

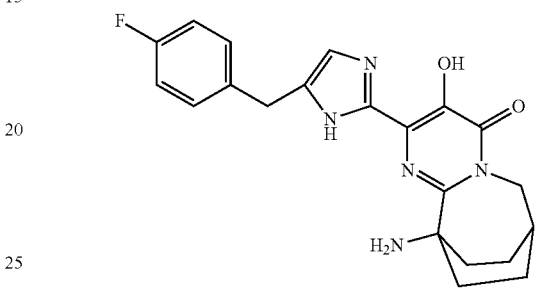

10-Amino-2-[4-[(4-fluorophenyl)methyl]-1H-imidazol-2-yl]-7,8,9,10-tetrahydro-3-hydroxy-7,10-ethanopyrimido[1,2-a]azepin-4(6H)-one To a solution of benzyl(3-(benzyloxy)-2-(4-chloro-5-(4-fluorobenzyl)-1H-imidazol-2-yl)-4-oxo-6,7,8,9-tetrahydro-7,10-ethanopyrimido[1,2-a]azepin-10(4H)-yl)carbamate, Intermediate 6 (60 mg, 0.092 mmol) in MeOH (3 mL) was added formic acid (0.100 mL, 2.65 mmol) followed by 10% Pd/C (98 mg, 0.092 mmol) and the mixture stirred at 40° C. for 3 h. After cooling to room temperature, the mixture was filtered through a pad of celite and concentrated. The mixture was then treated with sat. NaHCO$_3$, extracted with dichloromethnae (×4), dried (Na$_2$SO$_4$), filtered and concentrated to afford the title compound (30 mg, 83% yield) as a light purple solid. $^1$H NMR (500 MHz, DMSO-d$_6$) δ ppm 1.53-1.60 (m, 2H), 1.73-1.81 (m, 6H), 2.37 (br. s., 1H), 2.51-2.54 (m, 2H), 3.93-3.99 (m, 2H), 4.01 (d, J=3.66 Hz, 2H), 7.10-7.17 (m, 3H), 7.30 (dd, J=8.24, 5.80 Hz, 2H). LCMS (M+H)=396.13.

Example 2

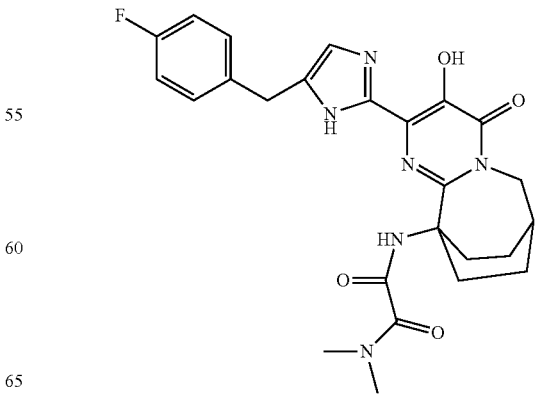

N'-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-N,N-dimethylethanediamide To a stirred solution of 10-amino-2-(4-(4-fluorobenzyl)-1H-imidazol-2-yl)-3-hydroxy-7,8,9,10-tetrahydro-7,10-ethanopyrimido[1,2-a]azepin-4(6H)-one, Example 1 (27 mg, 0.068 mmol) and 2-(dimethylamino)-2-oxoacetic acid (11.99 mg, 0.102 mmol) in DMF (3 mL) was added N,N-diisopropylethylamine (0.061 mL, 0.35 mmol), DMAP (1.668 mg, 0.014 mmol) and HATU (38.9 mg, 0.102 mmol) and the resulting mixture stirred at room temp for 3 h. The mixture was then concentrated and purified by preparative HPLC to afford the title compound (6 mg, 8% yield) as an off-white solid. $^1$H NMR (500 MHz, CDCl$_3$) δ ppm 1.63-1.77 (m, 2H), 1.93-1.98 (m, 2H), 2.29-2.38 (m, 4H), 2.50 (br. s., 1H), 3.00 (s, 3H), 3.17 (s, 3H), 4.03 (s, 2H), 4.14 (s, 2H), 6.82 (br. s., 1H), 7.00 (t, J=8.39 Hz, 1H), 7.21-7.27 (m, 3H), 7.70 (s, 1H). LCMS (M+H)=495.20.

Example 3

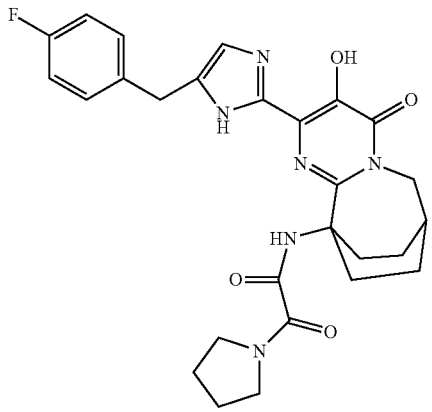 [SMILES: O=C(NC12CCC(CC1)Cn1c2nc(-c2ncc(Cc3ccc(F)cc3)[nH]2)c(O)c1=O)C(=O)N1CCCC1]

N-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-2-oxo-2-(pyrrolidin-1-yl)acetamide White solid (20 mg, 38% yield). $^1$H NMR (500 MHz, CDCl$_3$) δ ppm 9.0 (1H, br. s.), 7.1-7.2 (3H, m), 7.0 (3H, t, J=8.55 Hz), 4.1 (4H, br. s.), 3.4-3.6 (3H, m), 2.5 (1H, br. s.), 2.2-2.4 (2H, m), 2.1-2.2 (2H, m), 2.0-2.1 (3H, m), 1.8-1.9 (3H, m), 1.5-1.7 (3H, m). LCMS (M+H)=521.53.

Example 4

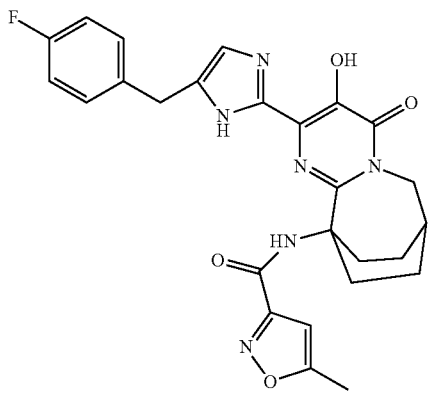 [SMILES: Cc1cc(C(=O)NC23CCC(CC2)Cn2c3nc(-c3ncc(Cc4ccc(F)cc4)[nH]3)c(O)c2=O)no1]

N-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-5-methyl-1,2-oxazole-3-carboxamide To a solution of 10-amino-2-(4-(4-fluorobenzyl)-1H-imidazol-2-yl)-3-hydroxy-7,8,9,10-tetrahydro-7,10-ethanopyrimido[1,2-a]azepin-4(6H)-one, Example 1 (30 mg, 0.076 mmol) in CH$_2$Cl$_2$ (3 mL) was added triethylamine (0.063 mL, 0.455 mmol) followed by 5-methylisoxazole-3-carbonyl chloride (55.2 mg, 0.379 mmol) and the resulting mixture stirred at room temperature. After 16 h the reaction mixture was concentrated to give the crude product which was treated with 2M dimethylamine/MeOH (0.5 mL) in MeOH (2 mL) at 60° C. for 2 h. The mixture was then cooled and purified by preparative HPLC to afford the title compound (15 mg, 39%) as a white solid. $^1$H NMR (500 MHz, DMSO-d$_6$) δ ppm 13.4 (1H, br. s.), 9.0 (1H, s), 7.4 (1H, br. s.), 7.4 (2H, dd, J=8.24, 5.80 Hz), 7.2 (2H, t, J=8.85 Hz), 6.6 (1H, s), 4.1 (2H, d, J=3.36 Hz), 4.1 (2H, s), 2.7-2.8 (2H, m), 2.5 (1H, br. s.), 2.0-2.0 (2H, m), 1.9-1.9 (2H, m), 1.7-1.8 (2H, m). LCMS (M+H)=505.49.

Example 5

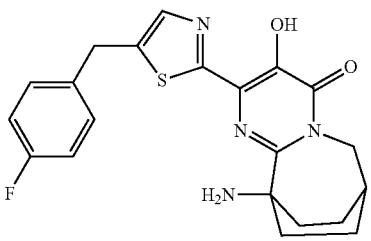 [SMILES: NC12CCC(CC1)Cn1c2nc(-c2ncc(Cc3ccc(F)cc3)s2)c(O)c1=O]

10-Amino-3-(benzyloxy)-2-(5-(4-fluorobenzyl)-1,3-thiazol-2-yl)-7,8,9,10-tetrahydro-7,10-ethanopyrimido[1,2-a]azepin-4(6H)-one To a solution of benzyl (3-(benzyloxy)-2-(5-(4-fluorobenzyl)-1,3-thiazol-2-yl)-4-oxo-6,7,8,9-tetrahydro-7,10-ethanopyrimido[1,2-a]azepin-10(4H)-yl)carbamate Intermediate 8 (60 mg, 0.094 mmol) in methanol (3 mL) was added 1N HCl (0.104 mL, 0.104 mmol) followed by Pd/C (10.03 mg, 9.42 μmol) and the resulting mixture was stirred under a hydrogen atmosphere for 3 h. The catalyst was removed by filtration and the mixture concentrated then diluted with dichloromethane (3 mL), treated with 48% HBr (0.2 mL) and stirred at room temperature for 16 h. The mixture was concentrated and the crude product was triturated with ethyl acetate/hexane, filtered and dried under high vacuum to afford the title compound HBr salt 0.102 mL, 1.885 mmol) as a dark brown solid. $^1$H NMR (500 MHz, DMSO-d$_6$) δ ppm 7.97 (1H, s), 7.36 (2H, dd, J=8.70, 5.65 Hz), 7.16-7.20 (2H, m), 4.32 (2H, s), 4.05 (2H, d, J=3.36 Hz), 2.46 (1H, br. s.), 2.08-2.16 (2H, m), 1.96-2.04 (2H, m), 1.81-1.89 (2H, m), 1.70-1.79 (2H, m). LCMS (M+H)=414.18.

Example 6

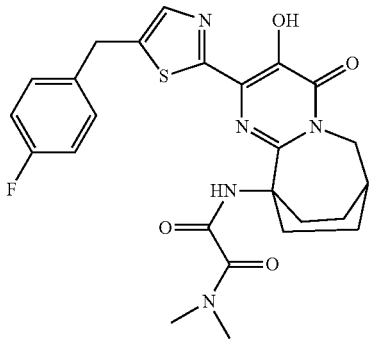 [SMILES: CN(C)C(=O)C(=O)NC12CCC(CC1)Cn1c2nc(-c2ncc(Cc3ccc(F)cc3)s2)c(O)c1=O]

N'-(2-(5-(4-Fluorobenzyl)-1,3-thiazol-2-yl)-3-hydroxy-4-oxo-6,7,8,9-tetrahydro-7,10-ethanopyrimido[1,2-a]azepin-10(4H)-yl)-N,N-dimethylethanediamide To a stirred solution of 10-amino-3-(benzyloxy)-2-(5-(4-fluorobenzyl)-1,3-thiazol-2-yl)-7,8,9,10-tetrahydro-7,10-ethanopyrimido[1,2-a]azepin-4(6H)-one, Example 5 (35 mg, 0.085 mmol) in DMF (2 mL) was added 2-(dimethylamino)-2-oxoacetic acid (19.87 mg, 0.170 mmol), N,N-diisoproplylethylamine (0.119 mL, 0.679 mmol), HATU (64.5 mg, 0.170 mmol) and DMAP (5.18 mg, 0.042 mmol) and the resulting mixture stirred at room temperature for 16 h. The mixture was purified by preparative HPLC to afford the title compound (7 mg, 0.013 mmol, 15.32% yield) as a light green solid. $^1$H NMR (400 MHz, DMSO-d$_6$) δ ppm 11.17 (1H, br. s.), 9.04 (1H, br. s.), 7.87 (1H, br. s.), 7.36 (2H, dd, J=8.16, 5.65 Hz), 7.19 (2H, t, J=8.78 Hz), 4.29 (2H, s), 4.06 (2H, d, J=3.51 Hz), 3.04 (3H, s), 2.87 (3H, s), 2.33-2.45 (3H, m), 2.03-2.14 (2H, m), 1.79-1.90 (2H, m), 1.60-1.71 (2H, m). LCMS (M+H)=512.01.

Example 7

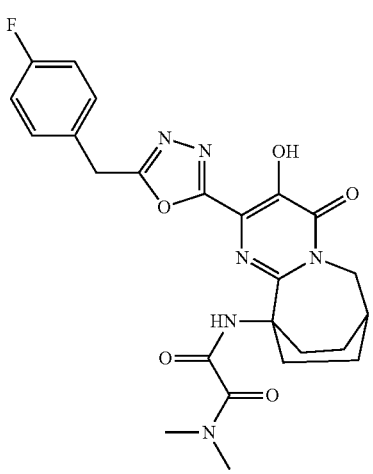 [SMILES: CN(C)C(=O)C(=O)NC12CCC(CC1)Cn1c2nc(-c2nnc(Cc3ccc(F)cc3)o2)c(O)c1=O]

N'-(2-(5-(4-Fluorobenzyl)-1,3,4-oxadiazol-2-yl)-3-hydroxy-4-oxo-6,7,8,9-tetrahydro-7,10-ethanopyrimido[1,2-a]azepin-10(4H)-yl)-N,N-dimethylethanediamide To a solution of 10-amino-2-(5-(4-fluorobenzyl)-1,3,4-oxadiazol-2-yl)-3-hydroxy-7,8,9,10-tetrahydro-7,10-ethanopyrimido[1,2-a]azepin-4(6H)-one, Intermediate 12 (20 mg, 0.042 mmol) in DMF (1.5 mL) was added 2-(dimethylamino)-2-oxoacetic acid (9.79 mg, 0.084 mmol), N,N-dissopropylethylamine (0.044 mL, 0.251 mmol), HATU (31.8 mg, 0.084 mmol) and DMAP (5.11 mg, 0.042 mmol) and the resulting mixture stirred at room temp for 3 h and then purified by preparative HPLC to afford the title compound (5 mg, 9.47 µmol, 22.64% yield) as a purple solid. $^1$H NMR (500 MHz, CDCl$_3$) δ ppm 11.10 (1H, br. s.), 9.60 (1H, s), 7.54 (2H, dd, J=8.39, 5.34 Hz), 7.10 (2H, t, J=8.55 Hz), 4.35 (2H, s), 4.24 (2H, br. s.), 3.44 (3H, s), 3.13 (3H, s), 2.99-3.08 (3H, m), 2.54 (1H, br. s.), 2.03-2.13 (2H, m), 1.85-1.94 (2H, m), 1.72-1.81 (2H, m). LCMS (M+H)+=497.18.

Example 8

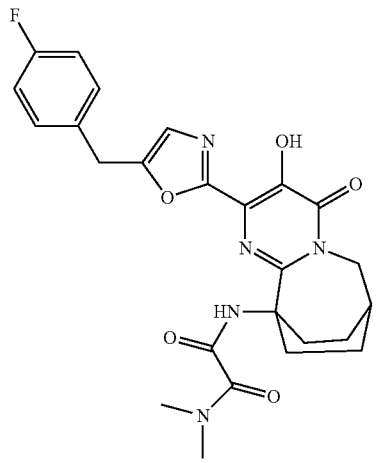 [SMILES: CN(C)C(=O)C(=O)NC12CCC(CC1)Cn1c2nc(-c2ncc(Cc3ccc(F)cc3)o2)c(O)c1=O]

N'-(4-(5-(4-Fluorobenzyl)-1,3-oxazol-2-yl)-3-hydroxy-4-oxo-6,7,8,9-tetrahydro-7,10-ethanopyrimido[1,2-a]azepin-10(4H)-yl)-N,N-dimethylethanediamide To a solution of N'-(3-(benzyloxy)-2-(5-(4-fluorobenzyl)-1,3-oxazol-2-yl)-4-oxo-6,7,8,9-tetrahydro-7,10-ethanopyrimido[1,2-a]azepin-10(4H)-yl)-N,N-dimethylethanediamide, Intermediate 17 (60 mg, 0.102 mmol) in CH$_2$Cl$_2$ (3 mL) was added TFA (1 mL, 12.98 mmol) and the resulting mixture heated at 40° C. for 16 h. The mixture was concentrated in vacuo and purified by preparative HPLC to afford the title compound (23 mg, 0.046 mmol, 45.3% yield) as a white solid. $^1$H NMR (500 MHz, CDCl$_3$) δ ppm 10.84 (1H, br. s.), 9.74 (1H, s), 7.45 (2H, dd, J=8.55, 5.49 Hz), 7.08 (2H, t, J=8.70 Hz), 6.97 (1H, s), 4.23 (2H, d, J=3.66 Hz), 4.13 (2H, s), 3.43 (3H, s), 3.11 (3H, s), 3.01-3.09 (2H, m), 2.52 (1H, br. s.), 2.02-2.12 (2H, m), 1.84-1.92 (2H, m), 1.72-1.80 (2H, m). LCMS (M+H)=496.28.

Example 9

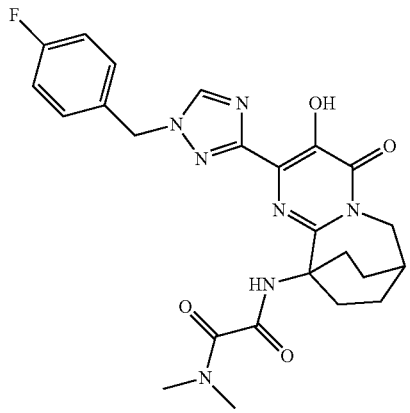 [SMILES: CN(C)C(=O)C(=O)NC12CCC(CC1)Cn1c2nc(-c2ncn(Cc3ccc(F)cc3)n2)c(O)c1=O]

N'-[2-[1-[(4-Fluorophenyl)methyl]-1H-1,2,4-triazol-3-yl]-6,7,8,9-tetrahydro-3-hydroxy-4-oxo-7,10-ethanopyrimido[1,2-a]azepin-10(4H)-yl]-N,N-dimethyl-ethanediamide $^1$H NMR (400 MHz, CDCl$_3$) δ ppm 9.61 (1H, br. s.), 8.25 (1H, br. s.), 7.45 (2H, br. s.), 7.13 (2H, t, J=7.7 Hz), 5.46 (2H, br. s.), 4.22 (2H, br. s.), 3.35 (3H, s), 3.06 (3H, br. s.), 2.97 (2H, br. s.), 2.52 (1H, br. s.), 2.05 (2H, br. s.), 1.94 (2H, br. s.), 1.75 (2H, br. s.); $^{19}$F NMR (376 MHz, CDCl$_3$) δ ppm −111.90 (1F, s); LCMS (ES+, (M+H)$^+$) m/z 496.1.

Example 10

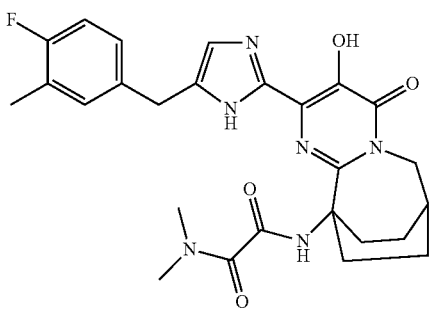 [SMILES: Cc1cc(Cc2cnc(-c3nc4n(c(=O)c3O)CC3CCC4(NC(=O)C(=O)N(C)C)CC3)[nH]2)ccc1F]

N'-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-N,N-dimethyl-ethanediamide trifluoroacetate salt $^1$H NMR (400 MHz, CDCl$_3$) δ ppm 7.60 (br. s., 1H), 7.03-7.14 (m, 2H), 6.95 (t, J=8.78 Hz, 1H), 6.87 (s, 1H), 4.15 (d, J=3.01 Hz, 2H), 4.03 (s, 2H), 3.18 (s, 3H), 3.03 (s, 3H), 2.53 (br. s., 1H), 2.37-2.47 (m, 2H), 2.27-2.37 (m, 2H), 2.25 (s, 3H), 1.91-2.04 (m, 2H), 1.73 (br. s., 2H); $^{19}$F NMR (376 MHz, CDCl$_3$) δ ppm −75.65 (s, 3F), −119.63 (s, 1F); LCMS (ES+, (M+H)$^+$) m/z 509.16.

Example 11

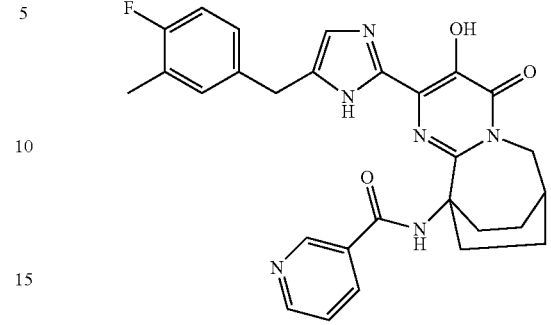

N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-3-pyridinecarboxamide trifluoroacetate salt $^1$H NMR (400 MHz, CDCl$_3$) δ ppm 11.42 (br. s., 1H), 9.34 (d, J=3.76 Hz, 1H), 8.39 (d, J=8.03 Hz, 1H), 7.78 (dd, J=8.41, 5.14 Hz, 1H), 7.09-7.19 (m, 2H), 7.08 (s, 1H), 6.96 (t, J=8.91 Hz, 1H), 4.25 (br. s., 2H), 4.17 (br. s., 2H), 3.07-3.27 (m, 2H), 2.56 (br. s., 1H), 2.25 (s, 3H), 2.09-2.21 (m, 2H), 1.92-2.04 (m, 2H), 1.78-1.91 (m, 2H); $^{19}$F NMR (376 MHz, CDCl$_3$) δ ppm −75.40 (s, 3F), −119.20 (s, 1F); LCMS (ES+, (M+H)$^+$) m/z 515.1.

Example 12

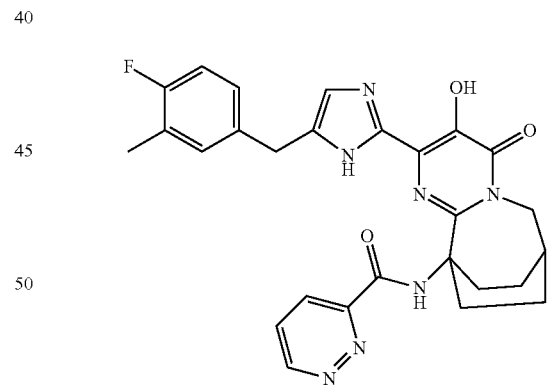

N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-3-pyridazinecarboxamide trifluoroacetate salt $^1$H NMR (400 MHz, CDCl$_3$) δ ppm 10.95 (br. s., 1H), 9.55 (s, 1H), 8.76 (d, J=7.78 Hz, 1H), 8.66 (d, J=5.52 Hz, 1H), 7.82-7.91 (m, 1H), 6.79-6.97 (m, 3H), 6.44 (s, 1H), 4.17 (br. s., 2H), 3.78 (br. s., 2H), 2.79-2.94 (m, 2H), 2.59 (br. s., 1H), 2.30-2.45 (m, 2H), 2.22 (s, 3H), 1.96-2.10 (m, 2H), 1.69-1.84

(m, 2H); ¹⁹F NMR (376 MHz, CDCl₃) δ ppm −75.81 (br. s., 3F), −120.29 (br. s., 1F); LCMS (ES+, (M+H)⁺) m/z 516.0.

Example 13

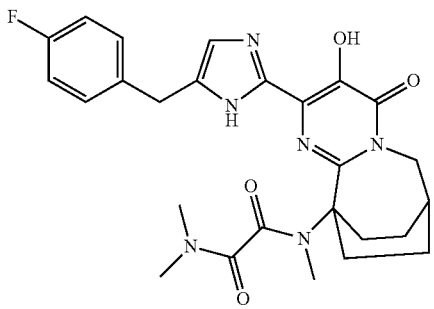 [SMILES: CN(C)C(=O)C(=O)N(C)C12CCC(CC1)Cn1c2nc(-c2ncc(Cc3ccc(F)cc3)[nH]2)c(O)c1=O]

N-[2-[4-[(4-Fluorophenyl)methyl]-1H-imidazol-2-yl]-6,7,8,9-tetrahydro-3-hydroxy-4-oxo-7,10-ethanopyrimido[1,2-a]azepin-10(4H)-yl]-N,N',N'-trimethyl-ethanediamide trifluoroacetate salt ¹H NMR (400 MHz, CDCl₃) δ ppm 7.23-7.33 (m, 2H), 6.96-7.07 (m, 3H), 4.10 (s, 2H), 3.69 (br. s., 1H), 3.41 (br. s., 1H), 3.08 (s, 3H), 3.05 (s, 3H), 3.01 (s, 3H), 2.53 (br. s., 1H), 1.99-2.17 (m, 4H), 1.83 (br. s., 2H), 1.60 (br. s., 2H); ¹⁹F NMR (376 MHz, CDCl₃) δ ppm −75.70 (br. s., 3F), −115.73 (br. s., 1F); LCMS (ES+, (M+H)⁺) m/z 509.0.

Example 14

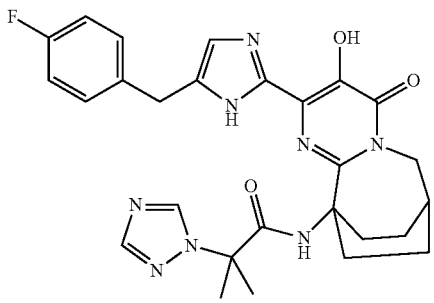 [SMILES: CC(C)(C(=O)NC12CCC(CC1)Cn1c2nc(-c2ncc(Cc3ccc(F)cc3)[nH]2)c(O)c1=O)n1cncn1]

N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-alpha,alpha-dimethyl-1H-1,2,4-triazole-1-acetamide trifluoroacetate salt ¹H NMR (400 MHz, CDCl₃) δ ppm 8.48 (s, 1H), 7.97 (s, 1H), 7.34 (s, 1H), 7.10 (s, 1H), 7.05 (d, J=7.03 Hz, 1H), 6.98-7.03 (m, 1H), 6.95 (t, J=8.78 Hz, 1H), 4.16 (d, J=3.51 Hz, 2H), 4.07 (s, 2H), 2.43-2.55 (m, 3H), 2.24 (d, J=1.51 Hz, 3H), 1.86-1.98 (m, 4H), 1.87 (br. s., 6H), 1.60-1.73 (m, 2H); ¹⁹F NMR (376 MHz, CDCl₃) δ ppm −75.78 (br. s., 3F), −119.54 (s, 1F); LCMS (ES+, (M+H)⁺) m/z 547.2.

Example 15

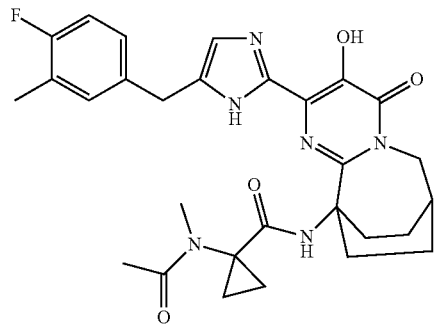 [SMILES: CC(=O)N(C)C1(C(=O)NC23CCC(CC2)Cn2c3nc(-c3ncc(Cc4ccc(F)c(C)c4)[nH]3)c(O)c2=O)CC1]

1-(Acetylmethylamino)-N-[2-[4-[(4-fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-cyclopropanecarboxamide trifluoroacetate salt ¹H NMR (400 MHz, CDCl₃) δ ppm 8.49 (s, 1H), 7.05-7.14 (m, 2H), 7.02 (s, 1H), 6.94 (q, J=8.55 Hz, 1H), 4.29-4.43 (m, 1H), 3.99-4.20 (m, 3H), 3.00 (s, 3H), 2.41-2.54 (m, 1H), 2.24 (s, 6H), 1.97 (br. s., 4H), 1.77 (br. s., 2H), 1.60 (br. s., 4H), 1.15-1.40 (m, 1H), 0.80-0.92 (m, 1H); ¹⁹F NMR (376 MHz, CDCl₃) δ ppm −76.28 (br. s., 3F), −120.63 (s, 1F); LCMS (ES+, (M+H)⁺) m/z 549.1.

Example 16

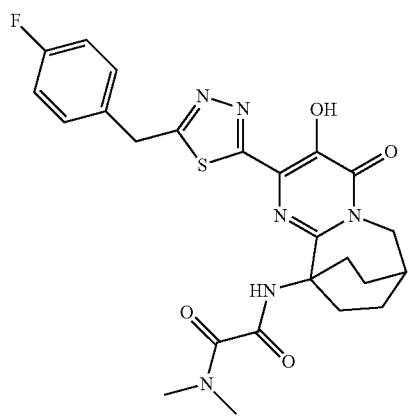 [SMILES: CN(C)C(=O)C(=O)NC12CCC(CC1)Cn1c2nc(-c2nnc(Cc3ccc(F)cc3)s2)c(O)c1=O]

N'-[2-[5-[(4-Fluorophenyl)methyl]-1,3,4-thiadiazol-2-yl]-6,7,8,9-tetrahydro-3-hydroxy-4-oxo-7,10-ethanopyrimido[1,2-a]azepin-10(4H)-yl]-N,N-dimethyl-ethanediamide ¹H NMR (400 MHz, CDCl₃) δ ppm 9.40 (1H, s), 7.30-7.38 (2H, m), 7.07 (2H, t, J=8.5 Hz), 4.48 (2H, s), 4.22 (2H, d, J=3.8 Hz), 3.40 (3H, s), 3.05 (3H, s), 2.94 (2H, ddd, J=14.2, 9.4, 5.3 Hz), 2.52 (1H, br. s.), 1.98-2.09 (2H, m), 1.82-1.93

(2H, m), 1.76 (2H, d, J=14.1 Hz); $^{19}$F NMR (376 MHz, CDCl$_3$) δ ppm −114.62 (1F, s); LCMS (ES+, (M+H)$^+$) m/z 513.1.

Example 17

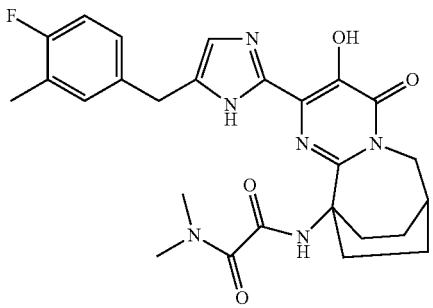 [SMILES: Cc1cc(Cc2cnc(-c3nc4n(c(=O)c3O)CC3CCC4(NC(=O)C(=O)N(C)C)CC3)[nH]2)ccc1F]

N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-N,N',N'-trimethyl-ethanediamide trifluoroacetate salt $^1$H NMR (400 MHz, CDCl$_3$) δ ppm 6.89-7.17 (m, 4H), 4.07 (s, 2H), 3.66 (br. s., 1H), 3.41 (br. s., 1H), 3.09 (s, 3H), 3.06 (s, 3H), 3.01 (s, 3H), 2.54 (br. s., 1H), 2.25 (s, 3H), 2.09 (br. s., 4H), 1.83 (br. s., 2H), 1.61 (br. s., 2H); $^{19}$F NMR (376 MHz, CDCl$_3$) δ ppm −75.75 (br. s., 3F), −119.93 (s, 1F); LCMS (ES+, (M+H)$^+$) m/z 523.17.

Example 18

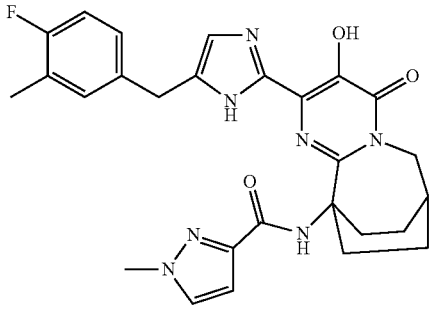 [SMILES: Cc1cc(Cc2cnc(-c3nc4n(c(=O)c3O)CC3CCC4(NC(=O)c4ccn(C)n4)CC3)[nH]2)ccc1F]

N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-1-methyl-1H-pyrazole-3-carboxamide TFA salt. $^1$H NMR (400 MHz, CDCl$_3$) δ ppm 8.92 (br. s., 1H), 7.40 (d, J=2.01 Hz, 1H), 7.03-7.14 (m, 2H), 6.96 (t, J=8.78 Hz, 1H), 6.76 (d, J=2.26 Hz, 1H), 6.63 (br. s., 1H), 4.03 (br. s., 5H), 3.94 (br. s., 2H), 2.54-2.68 (m, 2H), 2.47-2.54 (m, 1H), 2.27 (br. s., 5H), 2.01 (br. s., 2H), 1.64 (br. s., 2H); $^{19}$F NMR (376 MHz, CDCl$_3$) δ ppm −75.69 (br. s., 3F), −119.87 (br. s., 1F); LCMS (ES+, (M+H)$^+$) m/z 518.1.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

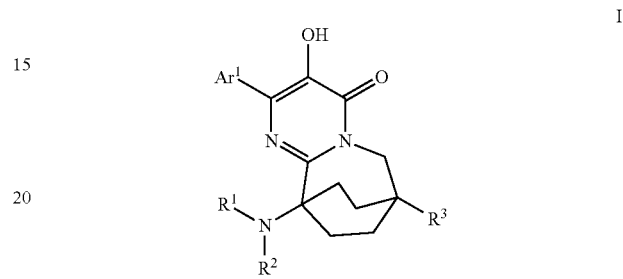

where:
R$^1$ is hydrogen, alkyl, alkylCO, (tetrahydropyranyl)CO, ((Ar$^2$)alkyl)CO, ((Ar$^2$)cycloalkyl)CO, (Ar$^2$)CO, CO$_2$R$^4$, CON(R$^5$)(R$^6$), COCO$_2$R$^4$, or COCON(R$^5$)(R$^6$);
R$^2$ is hydrogen or alkyl;
R$^3$ is hydrogen;
R$^4$ is hydrogen, alkyl, or benzyl;
R$^5$ is hydrogen, alkyl, cycloalkyl, haloalkyl, hydroxyalkyl, alkoxyalkyl aminoalkyl, alkylaminoalkyl, dialkylaminoalkyl, or alkylCO;
R$^6$ is hydrogen, alkyl, cycloalkyl, haloalkyl, hydroxyalkyl, alkoxyalkyl aminoalkyl, alkylaminoalkyl, dialkylaminoalkyl, or alkylCO;
or N(R$^5$)(R$^6$) taken together is azetidinyl, pyrrolidinyl, piperidinyl, piperazinyl, or morpholinyl, and is substituted with 0-3 substituents selected from halo and alkyl;
Ar$^1$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, or pyrrolyl; Ar$^1$ is substituted with 1 benzyl moiety which is further substituted with 0-3 substituents selected from halo and alkyl; and Ar$^1$ is substituted with 0-2 alkyl substituents; and
Ar$^2$ is tetrazolyl, triazolyl, oxadiazolyl, thiadiazolyl, imidazolyl, oxazolyl, thiazolyl, pyrazolyl, isoxazolyl, isothiazolyl, pyrrolyl, furanyl, thienyl, pyridinyl, pyridazinyl, pyrimidinyl, pyrazinyl, or hydroxypyridinyl, and is substituted with 0-3 substituents selected from the group consisting of oxo, halo, cyano, benzyl, alkyl, alkoxy, N(R$^5$)(R$^6$), CO$_2$R$^4$, and CON(R$^5$)(R$^6$);
or a pharmaceutically acceptable salt thereof.
2. A compound of claim 1 where:
R$^1$ is hydrogen, ((Ar$^2$)alkyl)CO, ((Ar$^2$)cycloalkyl)CO, (Ar$^2$)CO, or COCON(R$^5$)(R$^6$);
R$^2$ is hydrogen or alkyl;
R$^3$ is hydrogen;
R$^5$ is hydrogen, alkyl, or alkylCO;
R$^6$ is hydrogen or alkyl;
or N(R$^5$)(R$^6$) taken together is pyrrolidinyl;
Ar$^1$ is triazolyl, oxadiazolyl, thiadiazolyl, imidazolyl, oxazolyl, or thiazolyl; Ar$^1$ is substituted with 1 benzyl moiety which is further substituted with 1 halo substituent; and Ar² is triazolyl, pyrazolyl, isoxazolyl, pyridinyl, or pyridazinyl, and is substituted with 0-1 alkyl substituents;
or a pharmaceutically acceptable salt thereof.

3. A compound of claim 2 where
R¹ is hydrogen, ((Ar²)(dimethyl)methyl)CO, ((Ar²)cyclopropyl)CO, (Ar²)CO, or COCON(R⁵)(R⁶); R² is hydrogen or methyl; R³ is hydrogen; R⁵ is methyl or acetyl; R⁶ is methyl; or N(R⁵)(R⁶) taken together is pyrrolidinyl; Ar¹ is triazolyl, oxadiazolyl, thiadiazolyl, imidazolyl, oxazolyl, or thiazolyl; Ar¹ is substituted with 1 p-fluorobenzyl; and Ar² is triazolyl, methylpyrazolyl, methylisoxazolyl, pyridinyl, or pyridazinyl; or a pharmaceutically acceptable salt thereof.

4. A compound of claim 1 where R¹ is ((Ar²)alkyl)CO, ((Ar²)cycloalkyl)CO, (Ar²)CO, or COCON(R⁵)(R⁶).

5. A compound of claim 1 where R¹ is COCON(R⁵)(R⁶).

6. A compound of claim 1 where Ar¹ is triazolyl, oxadiazolyl, thiadiazolyl, imidazolyl, oxazolyl, or thiazolyl, and Ar¹ is substituted with 1 benzyl moiety which is further substituted with 0-3 substituents selected from halo and alkyl.

7. A compound of claim 6 where R¹ is ((Ar²)alkyl)CO, ((Ar²)cycloalkyl)CO, (Ar²)CO, or COCON(R⁵)(R⁶).

8. A compound of claim 7 where Ar² is pyrazolyl or isoxazolyl, and is substituted with 0-1, alkyl substituents.

9. A compound of claim 7 where R¹ is COCON(R⁵)(R⁶).

10. A compound of claim 9 where R¹ is COCONMe₂.

11. A compound of claim 1 selected from the group consisting of
10-Amino-2-[4-[(4-fluorophenyl)methyl]-1H-imidazol-2-yl]-7,8,9,10-tetrahydro-3-hydroxy-7,10-ethanopyrimido[1,2-a]azepin-4(6H)-one;
N'-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-N,N-dimethylethanediamide;
N-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-2-oxo-2-(pyrrolidin-1-yl)acetamide;
N-(2-(4-(4-Fluorobenzyl)-1H-imidazol-2-yl)-3-hydroxy-4-oxo-6,7,8,9-tetrahydro-7,10-ethanopyrimido[1,2-a]azepin-10(4H)-yl)-5-methyl-1,2-oxazole-3-carboxamide;
N'-(2-(5-(4-Fluorobenzyl)-1,3-thiazol-2-yl)-3-hydroxy-4-oxo-6,7,8,9-tetrahydro-7,10-ethanopyrimido[1,2-a]azepin-10(4H)-yl)-N,N-dimethylethanediamide;
N'-(2-(5-(4-Fluorobenzyl)-1,3,4-oxadiazol-2-yl)-3-hydroxy-4-oxo-6,7,8,9-tetrahydro-7,10-ethanopyrimido[1,2-a]azepin-10(4H)-yl)-N,N-dimethylethanediamide;
N'-(4-(5-(4-Fluorobenzyl)-1,3-oxazol-2-yl)-3-hydroxy-4-oxo-6,7,8,9-tetrahydro-7,10-ethanopyrimido[1,2-a]azepin-10(4H)-yl)-N,N-dimethylethanediamide;
N'-[2-[1-[(4-Fluorophenyl)methyl]-1H-1,2,4-triazol-3-yl]-6,7,8,9-tetrahydro-3-hydroxy-4-oxo-7,10-ethanopyrimido[1,2-a]azepin-10(4H)-yl]-N,N-dimethylethanediamide;
N'-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-N,N-dimethyl-ethanediamide;
N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-3-pyridinecarboxamide;
N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-3-pyridazinecarboxamide;
N-[2-[4-[(4-Fluorophenyl)methyl]-1H-imidazol-2-yl]-6,7,8,9-tetrahydro-3-hydroxy-4-oxo-7,10-ethanopyrimido[1,2-a]azepin-10(4H)-yl]-N,N',N'-trimethyl-ethanediamide;
N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-alpha,alpha-dimethyl-1H-1,2,4-triazole-1-acetamide;
N'-[2-[5-[(4-Fluorophenyl)methyl]-1,3,4-thiadiazol-2-yl]-6,7,8,9-tetrahydro-3-hydroxy-4-oxo-7,10-ethanopyrimido[1,2-a]azepin-10(4H)-yl]-N,N-dimethylethanediamide;
N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-N,N',N'-trimethyl-ethanediamide; and
N-[2-[4-[(4-Fluoro-3-methylphenyl)methyl]-1H-imidazol-2-yl]-6,7,8,9-tetrahydro-3-hydroxy-4-oxo-7,10-ethanopyrimido[1,2-a]azepin-10(4H)-yl]-1-methyl-1H-pyrazole-3-carboxamide;
or a pharmaceutically acceptable salt thereof.

12. A composition useful for treating HIV infection comprising a therapeutic amount of a compound of claim 1 and a pharmaceutically acceptable carrier.

13. A method for treating HIV infection comprising administering a therapeutically effective amount of a compound of claim 1, or a pharmaceutically acceptable salt thereof, to a patient in need thereof.

* * * * *